US008492431B2

(12) United States Patent
Smith-Swintosky et al.

(10) Patent No.: US 8,492,431 B2
(45) Date of Patent: Jul. 23, 2013

(54) USE OF BENZO-FUSED HETEROCYCLE SULFAMIDE DERIVATIVES FOR THE TREATMENT OF OBESITY

(75) Inventors: Virginia L. Smith-Swintosky, Hatfield, PA (US); Allen B. Reitz, Lansdale, PA (US)

(73) Assignee: Janssen Pharmaceutica, N.V., Beerse (BE)

( * ) Notice: Subject to any disclaimer, the term of this patent is extended or adjusted under 35 U.S.C. 154(b) by 580 days.

(21) Appl. No.: 11/611,938

(22) Filed: Dec. 18, 2006

(65) Prior Publication Data

US 2008/0027131 A1    Jan. 31, 2008

Related U.S. Application Data

(60) Provisional application No. 60/751,499, filed on Dec. 19, 2005.

(51) Int. Cl.
*A61K 31/35* (2006.01)

(52) U.S. Cl.
USPC ........................................................ 514/456

(58) Field of Classification Search
USPC ........................................................ 514/456
See application file for complete search history.

(56) References Cited

U.S. PATENT DOCUMENTS

| | | | |
|---|---|---|---|
| 2,527,861 A | 10/1950 | Walter | |
| 3,143,549 A | 8/1964 | Lafferty et al. | |
| 3,318,952 A | 5/1967 | Houlihan | |
| 3,383,414 A | 5/1968 | Houlihan | |
| 3,539,573 A | 11/1970 | Schmutz | |
| 3,621,096 A | 11/1971 | Prange et al. | |
| 4,513,006 A | 4/1985 | Maryanoff et al. | |
| 4,539,413 A | 9/1985 | Mouzin et al. | |
| 4,710,500 A | 12/1987 | Perregaard | |
| 4,804,663 A | 2/1989 | Kennis et al. | |
| 4,831,031 A | 5/1989 | Lowe, III et al. | |
| 4,879,288 A | 11/1989 | Warawa et al. | |
| 5,112,838 A | 5/1992 | Perregaard et al. | |
| 5,158,952 A | 10/1992 | Janssen et al. | |
| 5,192,785 A | 3/1993 | Lo et al. | |
| 5,194,446 A | 3/1993 | Lo et al. | |
| 5,212,326 A | 5/1993 | Meade | |
| 5,229,382 A | 7/1993 | Chakrabarti et al. | |
| 5,238,945 A | 8/1993 | Perregaard et al. | |
| 5,242,942 A | 9/1993 | Costanzo et al. | |
| 5,258,402 A | 11/1993 | Maryanoff | |
| 5,273,993 A | 12/1993 | Lo et al. | |
| 5,312,925 A | 5/1994 | Allen et al. | |
| 5,384,327 A | 1/1995 | Constanzo et al. | |
| 5,387,700 A | 2/1995 | Maryanoff et al. | |
| 5,731,348 A | 3/1998 | Gu et al. | |
| 5,753,693 A | 5/1998 | Shank | |
| 5,753,694 A | 5/1998 | Shank | |
| 5,760,007 A | 6/1998 | Shank et al. | |
| 5,780,650 A | 7/1998 | Furukawa et al. | |
| 5,935,933 A | 8/1999 | Shank et al. | |
| 5,998,380 A | 12/1999 | Ehrenberg et al. | |
| 6,071,537 A | 6/2000 | Shank | |
| 6,150,419 A | 11/2000 | Fairbanks et al. | |
| 6,187,338 B1 | 2/2001 | Caruso et al. | |
| 6,191,163 B1 | 2/2001 | Coltrell | |
| 6,211,241 B1 | 4/2001 | Islam et al. | |
| 6,319,903 B1 | 11/2001 | Carrazana et al. | |
| 6,322,503 B1 | 11/2001 | Sparhawk, Jr. | |
| 6,323,236 B2 | 11/2001 | McElroy | |
| 6,391,877 B1 | 5/2002 | Islam et al. | |
| 6,503,884 B1 | 1/2003 | Ehrenberg et al. | |
| 6,559,293 B1 | 5/2003 | Almarsson et al. | |
| 6,562,865 B1 | 5/2003 | Codd et al. | |
| 6,583,172 B1 | 6/2003 | Shank | |
| 6,627,653 B2 | 9/2003 | Plata-Salaman et al. | |
| 6,852,701 B2 | 2/2005 | Plata-Salaman et al. | |
| 6,852,738 B2 | 2/2005 | Jones et al. | |
| 6,949,518 B1 | 9/2005 | Chu | |
| 8,084,490 B2 | 12/2011 | McComsey et al. | |
| 2001/0008889 A1 | 7/2001 | Caruso et al. | |
| 2002/0015713 A1 | 2/2002 | Murdock et al. | |
| 2004/0073037 A1 | 4/2004 | Jones et al. | |
| 2004/0192690 A1 | 9/2004 | Buxton et al. | |
| 2004/0253223 A1 | 12/2004 | Rodriguez | |
| 2005/0148603 A1 | 7/2005 | Jimenez et al. | |
| 2005/0282887 A1 | 12/2005 | McComsey et al. | |
| 2006/0047001 A1 | 3/2006 | Parker et al. | |
| 2006/0241172 A1 | 10/2006 | Zhou et al. | |

(Continued)

FOREIGN PATENT DOCUMENTS

| | | |
|---|---|---|
| CA | 2416647 A | 1/2003 |
| DE | 1211166 | 2/1966 |

(Continued)

OTHER PUBLICATIONS

Scozzafava A, Mastrolorenzo A, and Supuran CT, "Modulation of carbonic anhydrase activity and its applications in therapy," Expert Opinion on Therapeutic Patents, May 2004, 14(5), 667-702.*
U.S. Appl. No. 11/611,961, filed Dec. 2006, Smith-Swintosky et al.*
Hauner H, "Managing type 2 diabetes mellitus in patients with obesity," Treatments in Endocrinology, 2004, 3(4), 223-232 (only abstract provided).*
Maryanoff et al.: Anticonvulsant O-Alkyl Sulfamates 2,3:4,5-Bis-O-(1-methylethylidene)-betas-D-fructopyranose Sulfamate and Related Compounds, J.Med. Chem., vol. 30, No. 5, 1987, pp. 880-887.
Maryanoff et al.: "Comparison of Sulfamates and Sulfamide Groups for the Inhibition of Carbonci Anhydrase-II by Using Topiratmate as a Structural Platform", J. Med. Chem, vol. 48, No. 6, 2004, pp. 1941-1947.

(Continued)

*Primary Examiner* — Paul Zarek
(74) *Attorney, Agent, or Firm* — Hal B. Woodrow

(57) ABSTRACT

The present invention is a method for the treatment of obesity, for promoting weight loss and/or suppressing appetite comprising administering to a subject in need thereof a therapeutically effective amount of one or more novel benzo-fused heterocycle sulfamide derivatives of formula (I) as herein defined.

10 Claims, No Drawings

U.S. PATENT DOCUMENTS

| | | |
|---|---|---|
| 2006/0270856 A1 | 11/2006 | Abdel-Magid |
| 2006/0276528 A1 | 12/2006 | Parker et al. |
| 2007/0293440 A1 | 12/2007 | Smith Swintosky et al. |
| 2007/0293476 A1 | 12/2007 | Smith Swintosky et al. |
| 2008/0027131 A1 | 1/2008 | Smith-Swintosky et al. |
| 2009/0138544 A1 | 5/2009 | Wegenkittl et al. |
| 2009/0182141 A1 | 7/2009 | Abdel-Magid et al. |
| 2009/0209634 A1 | 8/2009 | Smith-Swintosky et al. |
| 2009/0247617 A1 | 10/2009 | Abdel-Magid et al. |
| 2009/0247618 A1 | 10/2009 | Ballentine et al. |
| 2009/0318544 A1 | 12/2009 | Mehrman et al. |

FOREIGN PATENT DOCUMENTS

| | | |
|---|---|---|
| DE | 2022370 | 12/1971 |
| DK | 9800727 A | 5/1998 |
| EP | 0138441 B1 | 4/1985 |
| EP | 0483881 B1 | 5/1992 |
| EP | 490689 | 6/1992 |
| EP | 498770 | 8/1992 |
| EP | 503440 A1 | 9/1992 |
| EP | 478954 | 10/2000 |
| EP | 1056733 | 12/2000 |
| EP | 1118610 | 7/2001 |
| GB | 1087602 | 10/1967 |
| GB | 1111706 | 5/1968 |
| RU | 2246727 | 4/2004 |
| RU | 2226357 | 8/2004 |
| WO | WO 94/14827 A1 | 7/1994 |
| WO | WO 95/17406 A1 | 6/1995 |
| WO | WO 96/06822 A1 | 3/1996 |
| WO | WO 97/13510 A1 | 4/1997 |
| WO | WO 97/19682 A1 | 6/1997 |
| WO | WO 97/19919 | 6/1997 |
| WO | WO 97/35584 A1 | 10/1997 |
| WO | WO 98/00123 | 1/1998 |
| WO | WO 98/00124 A1 | 1/1998 |
| WO | WO 98/00130 A2 | 1/1998 |
| WO | WO 98/00131 A1 | 1/1998 |
| WO | WO 98/06708 A1 | 2/1998 |
| WO | WO 98/07447 A1 | 2/1998 |
| WO | WO 98/15270 | 4/1998 |
| WO | WO 99/44581 A2 | 9/1999 |
| WO | WO 99/62522 | 12/1999 |
| WO | WO 00/01376 A2 | 1/2000 |
| WO | WO 00/07583 A2 | 2/2000 |
| WO | WO 00/42995 A2 | 7/2000 |
| WO | WO 00/42996 A2 | 7/2000 |
| WO | WO 00/49017 | 8/2000 |
| WO | WO 00/50020 A2 | 8/2000 |
| WO | WO 00/54588 A1 | 9/2000 |
| WO | WO 00/61137 | 10/2000 |
| WO | WO 00/61139 A1 | 10/2000 |
| WO | WO 00/61140 A1 | 10/2000 |
| WO | WO 00/66109 A2 | 11/2000 |
| WO | WO 00/76493 A1 | 12/2000 |
| WO | WO 01/13904 A2 | 3/2001 |
| WO | WO 01/76576 A2 | 10/2001 |
| WO | WO 02/03984 | 1/2002 |
| WO | WO 02/07821 | 1/2002 |
| WO | WO 02/09694 | 2/2002 |
| WO | WO 02/30881 | 4/2002 |
| WO | WO 02/089785 | 11/2002 |
| WO | WO 02/096424 A1 | 12/2002 |
| WO | WO 2004/014352 | 2/2004 |
| WO | WO 2004/093912 A1 | 4/2004 |
| WO | WO 2004/092116 A1 | 10/2004 |
| WO | WO 2004/096771 A1 | 11/2004 |
| WO | WO 2004/098584 A1 | 11/2004 |
| WO | WO 2005/020917 A2 | 3/2005 |
| WO | WO 2006/007435 | 1/2006 |
| WO | WO 2006/007436 | 1/2006 |
| WO | WO 2006/010008 A1 | 1/2006 |
| WO | WO 2006/010750 A1 | 2/2006 |
| WO | WO 2006/023861 A1 | 3/2006 |
| WO | WO 2006/127184 | 11/2006 |
| WO | WO 2007/075695 | 7/2007 |
| WO | WO 2007/075698 | 7/2007 |
| WO | WO 2007/075717 | 7/2007 |
| WO | WO 2007/075751 | 7/2007 |
| WO | WO 2007/075752 | 7/2007 |
| WO | WO 2007/075833 | 7/2007 |
| WO | WO 2007/075834 | 7/2007 |
| WO | WO 2007/092086 | 8/2007 |
| WO | WO 2007/095615 | 8/2007 |
| WO | WO 2007/095618 | 8/2007 |
| WO | WO 2007/098486 | 8/2007 |
| WO | WO 2007/137167 | 11/2007 |
| WO | WO 2009/089210 | 7/2009 |
| WO | WO 2009/120191 | 10/2009 |
| WO | WO 2009/120192 | 10/2009 |

OTHER PUBLICATIONS

Levy RH et al., eds. Antiepileptic Drugs. 3$^{rd}$ ed. New York: Raven Press, 1989:85-102.
CA 835894-69-4 Sulfamide (1,3-benzodioxol-2-ylmethyl).
CA PLUS 835894-67-2 Sulfamic acid (1,3-benzodioxol-2-ylmethyl ester).
CA PLUS 835894-65-0 Sulfamide [(3, 4-dihydro-2H-1-benzopyran-2-yl) methyl].
CA PLUS 835894-63-8 Sulfamic acid (3,4-dihydro-2H-1-benzopyran-2-yl)methyl ester.
Penovich et al., "Weight Loss in Patients Receiving Topiramate for Intractable Epilepsy", 1994, Neurology 44 (Suppl. 2) Abstract 309P, 46$^{th}$ Annual Meeting of the American Academy of Neurology, Washington, D.C.
PCT International Search Report, PCT/US2005/029814, Nov. 9, 2005, U.S. Appl. No. 11/209,122.
PCT International Search Report, PCT/US2005/021513, Sep. 27, 2005, U.S. Appl. No. 11/154,443.
PCT International Search Report, PCT/US2005/021515, Jun. 16, 2005, U.S. Appl. No. 11/154,386.
U.S. Appl. No. 11/154,443, Maryanoff Bruce E.
U.S. Appl. No. 11/154,386, McComsey David F.
U.S. Appl. No. 11/209,122, Maryanoff Bruce E.
U.S. Appl. No. 11/611,961, Reitz Allen B.
U.S. Appl. No. 11/612,071, Reitz Allen B.
U.S. Appl. No. 11/612,146, Reitz Allen B.
U.S. Appl. No. 11/612,174, Smith-Swintosky.
U.S. Appl. No. 11/612,202, Reitz Allen B.
U.S. Appl. No. 11/612,222, Reitz Allen B.
U.S. Appl. No. 11/612,249, Reitz Allen B.
U.S. Appl. No. 11/673,705, Smith-Swintosky.
U.S. Appl. No. 11/673,709, Smith-Swintosky.
U.S. Appl. No. 11/673,713, Smith-Swintosky.
U.S. Appl. No. 11/673,723, Smith-Swintosky.
U.S. Appl. No. 11/673,977, Smith-Swintosky.
U.S. Appl. No. 11/673,987, Smith-Swintosky.
U.S. Appl. No. 11/673,998, Smith-Swintosky.
U.S. Appl. No. 11/674,011, Smith-Swintosky.
U.S. Appl. No. 11/674,021, Smith-Swintosky.
U.S. Appl. No. 11/677,717, Fawzy Nagy.
U.S. Appl. No. 60/883,442, Smith-Swintosky.
Scozzafava et al., "Modulation of carbonic anhydrase activity and its applications in therapy" Expert Opinion on Therapeutic Patents 2004, United Kingdom, vol. 4, No. 5, 2004, pp. 667-702.
PCT International Search Report, PCT/US2006/048681 dated Jul. 5, 2007.
Agrawal et al., Bioorganic and Medicinal Chemistry, 11(2003), pp. 5353-5362.
Casini et al., Bioorganic and Medicinal Chemistry Letters, 13(2003), pp. 841-845.
Pasorekova et al., Journal of Enzyme Inhibition and Medicinal Chemistry, Jun. 2004, vol. 19(3), pp. 199-229.
Supuran et al., Curr. Med. Chem.—Cardiovascular and Hematological Agents, 2004, 2, pp. 49-68.
Supuran et al., Curr. Med. Chem.—Imm., Endoc. & Metab Agents, 2001, 1, 61-97.
Supuran et al., Exp. Opin. Ther. Patents, (2000), 10(5), pp. 575-600.
Supuran et al., Exp. Opin. Ther. Patents, (200), 12(2), pp. 217-242, 2002.

Supuran et al., Medicinal Research Reviews, vol. 23, No. 2, pp. 146-189, 2003.
Thakur at al., Bioorganic and Medicinal Chemistry, 12(2004), pp. 789-793.
Aeberli, P. et al. "Neuropharmacological Investigation of N-Benzylsulfamides", Journal of Medicinal Chemistry, Jul. 1967, vol. 10, No. 4, pp. 636-642.
Ambrosini, P.J., Psychiatr. Serv. 2000, 51, 627-633.
American Diabetes Association, "Definition and Description of Diabetes Mellitus", Diabetes Care, Jan. 2006; p. S43-S48, vol. 29 Supplement 1.
Ananth, J., Psychother. Psychosom. 1998, 67, 61-70.
Angehagen, Mikael et al., "Does topiramate (TPM) have protective effects on astroglia cells and neurons in primary cortical cultures", Epilepsia, (1998) vol. 39, No. Suppl 6, pp. 44, XP000923162 abstract 2.050.
Ayata et al., "Suppression of cortical Spreading Depression in Migraine Prophylaxis", Ann Neurol 2006; 59:652-661.
Barry et al. Current status of the utilization of antiepilpetic treatments in mood, anxiety and aggression: drugs and devices, Jan. 2004, 35, 1.
Beck-Nielsen H., "In Vivo Glucose Metabolism, Insulin Secretion and, Insulin Action in Europids with Non-insulin-dependent Diabetes Mellitus (NIDDM) and Their First-degree Relatives", Diabet Med Sep. 1996;13(9 Suppl 6):S78-84.
Berman, R.M. et al., Depress. Anxiety 1997, 5, 154-164.
Besag et al. "Behavioural Effects of the New Anticonvulsants" Drug Safety, ADIS Press, Auckland, NZ, vol. 24, No. 7, 2001, pp. 513-536.
Breslau et al., "The impact of migraine. Epidemiology, risk factors, and co-morbidities" Neurology, 2001;56:S4-S12 (Abstract only).
Burton et al. Anti-epileptic drugs for pain management. Pain, Symptom, Control and Palliative Care, 2001, vol. 1, No. 2.
Cadieux, R.J., Am. Fam. Physician 1998, 58, 2059-2062.
Calabrese, J.R. et al., Eur. Neuropsychopharmacol. 1999, 9, S109-S112.
Calabresi et al., "Antiepileptic drugs in migraine: from clinical aspects to cellular mechanisms", TRENDS in Pharmacological Sciences, vol. 28, No. 4, 188-195 (2007).
Caumo A., "Insulin Sensitivity from Meal Tolerance Tests in Normal Subjects: A Minimal Model Index", J Clin Endocrinol Metab, 85(11):4396-402 2000.
Cavaletti G et al: "Experimental peripheral neuropathy induced in adult rats by repeated intraperitoneal administration of Taxal", Exper Neurol 133:64-72, 1995.
Chaplan SR et al: "Quantitative assessment of tactile allodynia in the rat paw". J Neurosci Meth, 53:55-63, 1994.
Crooke et al, Abstract, Topiramate Improves Glycemic Control Independent of Weight Loss in ob/ob Mice.diabetes. A Journal of the American Diabetes Association, Abstract Book 61$^{st}$ Scientific Sessions Friday, Jun. 22-Tuesday Jun. 26, 2001, 2158-PO, A513.
Demarest et al, Abstract, Topiramate Improves Glucose Tolerance and May Improve Insulin Sensitivity in Animal Models of Type 2 Diabetes Mellitus, diabetes, A Journal of the American Diabetes Association, Abstract Book 61st Scientific Sessions Friday, Jun. 22-Tuesday Jun. 26, 2001, 1254-P, A302.
Diamond et al, "Practical Approaches to Migraine Management", 2002, CNS Drugs, 16(6), pp. 385-403.
Dickenson et al. Neurobiology of neuropathic pain: mode of action of anticonvulsants. European Journal of Pain, 2002, 6 (Suppl. A): 51-60, 2002.
Dinneen S.F., "The Postprandial State: Mechanism of Glucose Intolerance", Diabet Med Aug. 1997;14 Suppl 3:S19-24.
Drach, B.S. et al.:"N-1,2,2,2,-tetra-chloroethyl-N',N'-dimethylsulphamide". Journal of Organic Chemistry of the USSR., vol. 13, No. 7, Jul. 1977, pp. 1289-1294, XP008067470.
Dressler et al., Benzodiazepine in geriatric patients . . . , Abstract, Anaesthesiologie und reanimation, 1996, vol. 21/5, pp. 136-138.
Drug Facts and Comparison (1995 Edition, pp. 1607).
Dursun, S.M. et al., "Accelerated weight loss after treating refractory depression with fluoxetine plus topiramate: possible mechanisms of action?", The Canadian Journal of Psychiatry, vol. 46, No. 3, pp. 287-288, 2001.

Edwards, K.R. et al, Efficacy and safety of topiramate in the treatment of painful diabetic neuropathy: a double-blind placebo-controlled study ADIS Title: Topiramate: therapeutic use: Neurogenic pain; In patients with diabetic neuropathy: Neurology 54 (Suppl. 3): 81 Apr. 11, 2000.
Edwards, et al., Evaluation of Topiramate in the Management of Painful Diabetic Neuropathy. Presented at: 18$^{th}$ Annual Meeting of the American Pain Society; 1998, Fort Lauderdale, FL.
Emancipator K., "Laboratory Diagnosis and Monitoring of Diabetes Mellitus", Am J Clin Pathol, 112(5):665-74 1999.
Erfurth, Andreas et al., "Bupropion as add-on strategy in difficult-to-treat bipolar depressive patients", Neuropsychobiology, vol. 45, No. Sup 1, pp. 33-36, 2002.
Fakhoury et al., Epilepsy Behav. Aug. 2007, abstract.
Flatters, SJL et al: "Acetyl-L-carnitine prevents and reduces paclitaxel-induced painful peripheralneuropathy", Neurosci Lett 397:219-223, 2006.
Gareri, P. et al, Progress in Neurobiology 61, 2000, 353-396.
Garonna, F. et al., "Topiramate in the treatment of overweight/obese binge eaters ADIS Title: Topiramate: therapeutic use; Obesity; In patient with binge eating disorders" International Journal of Neuropsychopharmacology 3(Suppl 1): 299: Jul. 2000 XP001030426 Bassano dG Vicenza Italy, whole document.
Ghaemi et al., Soc. of Bio. Psychiatry, (1999) vol. 45, 137-144.
Goldberg R.G., "Prevention of Type 2 Diabetes", Med Clin North Am, Jul. 1998;82(4):805-21.
Gorelick D A, "Pharmacological treatment" Recent Developments in Alcoholism, vol. 11, 1993, p. 413-427, XP00913482 p. 417.
Gorelick et al., Drugs 2004: 64(14), pp. 1547-1573.
Grond et al., "Weak Opiods—an educational substitute for morphine?", Current Opinion in Anaesthesiology, vol. 11, No. 5, 1998, pp. 559-565 XP00982759.
Groop L., "Characterization of the Prediabetic State", Am J Hypertension; Sep. 1997;10(9 Pt 2):172S-180S.
Guillaume et al., "Glial contribution to seizure: Carbonic anhydrase activity in epileptic mammalian brain" Epilepsia, 1991, vol. 32, No. 1, 1991, pp. 10-15.
Haffner S.M., "Impaired Glucose Tolerance, Insulin Resistance and Cardiovascular Disease", Diabetic Medicine, Aug. 1977;14 Suppl 3:S12-8.
Haffner S.M., "The Prediabetic Problem: Development of Non-Insulin-Dependent Diabetes Mellitus and Related Abnormalities", J Diabetes Complications, Mar.-Apr. 1997; 11(2):69-76.
Harrison's Principles of Internal Medicine, Isselbacher et al. eds. McGraw-Hill, Inc., New York, 1994, p. 69.
Harrison's Principles of Internal Medicine, vol. 2, 23d ed., Ed by Isselbacher, Braunwald, Wilson, Martin, Fauci and Kasper, McGraw-Hill Inc New York City, 1994, p. 2275.
Hatzinger, M. et al., Wien. Med. Wochenschr. 1999, 149, 511-514.
Headache Classification Committee of the International Headache Society. Cephalalgia 1988;8 Suppl 7:1-96.
Hering et al., "Sodium valproate in the treatment of cluster headache", Cephalalgia (Sep. 1989) 9(3) pp. 195-198.
Huisman, M. et al.:"Synthesis of N-(diemthylsulphamoyl)aldimines, a new type of aldimine derivative". Synthetic Communications, vol. 27, No. 6, 1997, pp. 945-952.
Jay et al., "Epilepsy, Migraine and EEG Abnormalities in Children: a Review & Hypothesis," Journal of Head and Face Pain, abstract, vol. 22, Issue 3, pp. 110-114, 1982.
Joffe, R.T. et al., Arch. Gen. Psychiatry 1993, 50, 397-393.
Johns Hopkins Clinical Trial of Topiramate for Cocaine Addiction (ClinicalTrials.gov), 2009.
Johnson, B A: "Progress in the development of topiramate for treating alcohol dependence: From a hypothesis to a proof-of-concept study" Alcoholism: Clinical and Experimental Research 2004 United States, vol. 28, No. 8, 2004, pp. 1137-1144.
Johnson, SA CNS Drugs, 2005. vol. 19, No. 1 0, pp. 873-896.
Kawasaki, "Structural and functional analysis of pancreatic islets preserved by pioglitazone in db/db mice", Am J Physiol Endocrinol Metab; 2004, p. E510-E518, doi 10.1152/ajpendo.00128.2004.
Keck, P et al, "Valproate and carbamazepine in the treatment of panic and post traumatic stress disorders, withdrawals states . . . " J Clin Psychopharm, vol. 12, No. 1, p. 36S-41S, 1992.

Kent, J.M., Lancet 2000, 355, 911-918.

Ketter, T.A. et al., J. Clin. Psychiatry 1995, 56, 471-475.

Keung W.M. et al, "Daidzin and daidzein suppress free-choice ethanol intake by Syrian golden hamsters" Proc Natl Acad Sci, vol. 90, p. 1008-10012, Nov. 1993.

Klinger et al., "Inhibition of carbonic anhydrase-II by sulfamate and sulfamide groups: An investigation involving direct thermodynamic binding measurements" Journal of Medicinal Chemistry, vol. 49, No. 12, Jun. 15, 2006, pp. 3496-3500.

Kohno, H. et al.: "A Novel Synthesis of Isoquinolines Containing an Electron Withdrawing Substitute". Heterocycles, vol. 51, No. 1, 1999, pp. 103-117, XP008052600.

Kralinsky E.A. Tramal in the treatment of pain in children with malignancies, Klinicka Onkologie, vol. 7, No. 6, 1994, pp. 182-185 (See English Abstract provided).

Kunkler et al., "Hippocampal Spreading Depression Bilaterally Activates the Caudal Trigeminal Nucleus in Roadent", Hippocampus 13:835-844 (2003).

Kuzniecky et al., "Topiramate increases cerebral GABA in healthy humans", Neurology (Aug. 1998) 51(2) pp. 627-629.

Kyowa Hakko, "Topiramate" Drugs of the Future, ES, Barcelona, vol. 21, No. 4, Jan. 1, 1996; p. 463-465.

Langtry H.D. et al, "Topiramate, A review of its pharmacodynamic and pharmacokinetic properties and clinical efficacy in the management of epilepsy" Drugs, (1997) 54/5 pp. 752-773, XP002179441.

Lydiard, R.B. et al., J. Clin. Psychiatry 1998, 59, Suppl. 18, 10-17.

Malatynska et al., "Dominant-submissive behavior as models of mania and depression", Neuroscience and Biobehavioral Review, 29 (2005) 715-737.

Malatynska et al., "Submissive behavior in mice as a test for antidepressant drug activity", Neuroscience and Biobehavioral Review, 82 (2005) 306-313.

Maryanoff, B.E.et al.: "Structure-Activity Studies on Anticonvulsant Sugar Sulphmates Related to Topiramate. Enhanced Potency with Cyclic Sulphate Derivatives". Journal of Medicinal Chemistry, vol. 41, No. 8, 1998, pp. 1315-1343.

Mathew, Ninan T., MD, et al, "Prophylaxis of Migraine, Transformed Migraine, and Cluster Headache with Topiramate" Headache (2002), (42)796-803.

Mathew, N. T. "Antiepileptic Drugs in Migraine Prevention", 2001, Headache, Nov./Dec. Suppl 2001, pp. S18-S24.

Mazzotta et al., J Headache Pain, 2004 5:S67-S70.

McElroy, S.L. et al., "A pilot trial of adjunctive topiramate in the treatment of bipolar disorder ADIS Title: Topiramate: therapeutic use; Bipolar disorder: A pilot trial of adjunctive treatment" retrieved from STN Database Accession No. 1998:39968 XP00217779443 Abstract & XXIST CINP Congress (Jul. 12, 1998) pp. 281 (Poster) University of Cincinnati College of Medicine, Cincinnati, OH.

Meldrum B. et al., "Excitatory amino acid neurotoxicity and neurodegenerative disease" TIPS, vol. 11, 1990, pp. 379-387, XP000915223.

Migraine: Treatments and drugs, by Mayo Clinic Staff, http://www.mayoclinic.com/health/migraineheadache/DS00120/DSECTION=treatments-and-drugs, 2009.

Moller, H.J. et al., Eur. Arch. Psychiatry Clin. Neurosci. 2000, 250, 57-68.

Moskowitz, M.A., "The Neurobiology of Vascular Head Pain", Annals of Neurology, vol. 16, Issue 2, pp. 157-168, 1984.

Mueller T I, "A double-blind, placebo-controlled pilot study of carbamazepine for the treatment of alcohol dependence", Alcoholism Clin Exp Res, vol. 21, No. 1, 1997, p. 86-92.

Mula et al., "The role of anticonvulsant drugs in anxiety disorders: a critical review of the evidence" Journal of Clinical Psychopharmacology, Williams and Wilkins, vol. 1.27, No. 3, 2007, pp. 263-272.

Myers, R.D., "New Drugs for the Treatment of Experimental Alcoholism", Alcohol, vol. 11, No. 6, 1994, p. 439-451.

Nemeroff, C.B., Depress. Anxiety 1996-1997, 4, 169-181.

Nickel et al., Journal of Affective Disorders, vol. 87(2-3), 2005, pp. 243-252.

Nies et al., Goodman & Gilman's the Pharmacological Basis of Therapeutics, 9th Edition, pp. 43-62, 1996.

Olesen et al., "Spreading Cerebral Oligemia in Classical- and Normal Cerebral Blood Flow in Common Migraine", Department of Neuromedicine, Rigshospitalet 2100 Copenhagen, Denmark, Jan. 28, 1982 (Headache 22:242-248, 1982).

Olson et al [Editors]. Remington's Pharmaceutical Sciences, pp. 420-425, 1980.

Osborne et al, Abstract, Topiramate Improves Glycemic Control and Triglycerides in Animal Models 1 page the Posters were presented at the American Diabetes Association Conference held Jun. 22-26 in Philadelphia, diabetes, A Journal of the American Diabetes Association, Abstract Book 61st Scientific Sessions Friday, Jun. 22-Tuesday Jun. 26, 2001, 1255-P, A302.

Ottman et al., "Comorbidity of migraine and epilepsy", Neurology, 1994;44: 2105 (Abstract only).

Pansare, S.V. et al.: "Intramolecular Imine Cross-Coupling in Dibenzylidine Sulphamides; synthesis of unsymmetrical 1,2-diaryl ethanediamines". Tetrahedron Letters, vol. 37, No. 16, Apr. 15, 1996, pp. 2859-2862 (2005).

Pascual D et al: "A cannabinoid agonist, WIN55,212-2, reduces neuropathic nocicipetion induced by paclitaxel in rats" Pain 118:23-34, 2005.

Perry et al. "Sumatriptan: An Updated Review of its Use in Migraine", 1998, Drugs, vol. 55, No. 6, pp. 889-922.

Pini et al., "Anti-Epileptic Drugs in the Preventive Treatment of Migraine Headache: a Brief Review", (J. Headache Pain, 2001, 2:13-19.

Polomano et al: "A painful peripheral neuropathy in the rat produced by the chemotherapeutic drug, paclitaxel", Pain, 94:293-304, 2001.

Prado Lima, P.A.S. et al., "Topiramate in treatment-refractory depression" retrieved from STN Database accession No. 1999:61852 XP002179442 Abstract & 11th World Congress of Psychiatry (Aug. 6, 1999), vol. 2,00.126.

Raguraman, et al., "Effects of topiramate in alcohol dependence [2]" Australian and New Zealand Journal of Psychiatry, 2005 Australia, vol. 39, No. 8, 2005, pp. 736-737.

Ramlo-Halsted BA, "The Natural History of Type 2 Diabetes", Primary Care Dec. 1999;26(4):771-89.

Reis et al. Craving decrease with topiramate in outpatient treatment for cocaine dependence: an open label trial, Rev Bras Psiquiatr 2008;30(2):132-5.

Rogaswki et al., Nature Medicine, vol. 10, No. 7, Jul. 2004, pp. 685-692.

Rogawski et al., Nature Reviews Neuroscience, vol. 5 (1), 2004, pp. 553-564.

Rost et al., The effect of tramadol and other analgesics on the pain..., Abstract, Arzneim-Forsch. 1978, vol. 28 (1a0 pp. 181-183).

Rouillon, F., Eur. Neuropsychopharmacol 1999, 9 Suppl. 3, S87-S92.

Rygula et al., "Anhedonia and motivational deficits in rats: Impact of chronic social stress", Behavioral Brain Research, 162 (2005) 127-134.

Sanacora, G. et al., "Impairment of GAB Aergic transmission in depression: New Insights from neuroimaging studies", Critical Reviews in Neurobiology, (2000) 14/1 pp. 23-45, XP001029967, whole document.

Shank et al., "Examination of two independent kinetic assays for determining the inhibition of carbonic anhydrases I and II: Structure-activity comparison of sulfamates and sulfamides" Chemical Biology and Drug Design, vol. 68, No. 2, 2006, pp. 113-119.

Sharma K, McCue P, Dunn SR. Am J Physiol Renal Physiol. Jun. 2003;284(6):F1138-44.

Silberstein et al., "Migraine & Epilepsy", www.myepilepsy.com, 2002.

Sofuoglu et al., CNS Drugs 2005: 19(1), pp. 13-25.

Soledade et al.:"Toward the control of Leptosphaeria Maculans Design, Synthesis, biological activity, and metabolism of potential detoxification inhibitors of the crucifer phytoalexin brassinin". Bioorganic & Medicinal Chemistry, vol. 14, No. 14, Apr. 17, 2006, pp. 4958-4979, XP005458688.

Stephen, Linda J. et al., "Lamotrigine and topiramate may be a useful combination", The Lancet, vol. 351, No. 9107, pp. 958-959, 1998.

Stephen, Linda J. et al., "Topiramate in Refractory Epilepsy: A Prospective Observational Study", Epilepsia, vol. 41, No. 8, pp. 977-980, 2000.

Stoll et al., Harvard Rev. Psychiatry, Jul./Aug. (1996), vol. 4, No. 2, 77-89.
Storey et al, "Topiramate in Migraine Prevention: A Double Blind, Placebo-Controlled Study", 2001, Headache, 41, pp. 968-975.
Ten Have, R. et al.:"Novel Synthesis of 4(5)-monosubstituted imidazoles via cycloaddition of tosylmethyl isocyanide to aldimines". Tetrahedron, vol. 53, No. 33, Aug. 18, 1997, pp. 11355-11368, XP004106007.
Tenovuo, O. "Central Acetylcholinesterase Inhibitors in the Treatment of Chronic Traumatic Brain Injury-Clinical Experience in 111 Patients". Progress in Neuro-Psychopharmacology and Biological Psychiatry 2005 US, vol. 29, No. 1, Jan. 2005,pp. 61067. XP002431412.
The Merck Manual (1987), Merck Sharp & Dohme Research Laboratories, Rahway, NJ XP002144176, pp. 1351-1356.
The Merck Manual, 1999, Merck Research, Whitehouse Station, NJ XP002224345, Diabetes Mellitus, pp. 165-177.
Topiramate retrieved from STN Database Accession No. 1998:2562 XP002179444 Abstract & R&D Focus Drug News, Jul. 27, 1998.
Traube, W. et al.:"Zur Kenntnis des Sulfamids". Berichte der Deutschen Chemischen Gesellschaft, vol. 56, 1923, pp. 1656-1663, XP002393747.
Uhart et al., Addiction Biology, 14, pp. 43-64, 2008.
Uys et al., CNS Neurol Disord Drug Targets, 7(5), 2008, pp. 482-491.
Van Amerigen et al. Antiepileptic drugs in the treatment of anxiety disorders: Role in Therapy, Drugs, 2004, 64(19), 2199-2220.
Vandi, A., et al.: "Synthesis and Properties of Some N-Substituted Sulphamides", Journal of Organic Chemistry, vol. 26, No. 4, Apr. 1961, pp. 1136-1138, XP002394144.
Von Seggern, Randal L., et al, "Efficacy of Topiramate in Migraine Prophylaxis: A Retrospective Chart Analysis" Headache (2002), (42)804-809.
Waugh et al., "Topiramate: As Monotherapy in Newly Diagnosed Epilepsy" CNS Drugs, vol. 17, No. 13, 2003, pp. 985-992.
Wauquier A et al, "Topiramate: A potent anticonvulsant I the Amygdala-Kindled Rat" Epilepsy Research, NJ, Elsevier Science Publishers, Amsterdam, vol. 24, No. 2, Jun. 1, 1996, p. 73-77, XP002042953.
WebMD Medical News Epilepsy Drugs Fights Migraine, 2002, www.webmd.com/migraine-headaches/news/20020923/epilepsydrug-fights-migraine.
Weib, G. et al.: "Herstellung und Reaktionen von N-Monoalkylamidosulfonylchloriden" Liebigs Annalen Der Chemie, vol. 729, Dec. 1969, pp. 40-51, XP002187581 (See English Abstract provided).
Wheeler et al., "Topiramate-treated cluster headache", Neurology (Jul. 1999) vol. 53, No. 1 pp. 234-236.
Wheeler S.D., "Antiepileptic Drug therapy in Migraine Headache", Current Treatment Options Neurology, Sep. 2002; 4(5):383-394.
Wheeler, "Significance of migrainouse features in cluster headache", Headache (1998) 38/7 pp. 547-551.
Whitehead, C.W. et al.: "Diuretics. II. Alkoxymercuration oby mixed anion sales of mercury". Journal of the American Chemical Society, vol. 80, No. 9, May 5, 1958, pp. 2182-2185, XP002393746.
Williams, Jr., J.W., et al., Ann. Intern. Med. 2000, 132, 743-756.
Winhusen et al. Drug and Alcohol Dependence 91 (207) 131-148, 2007.
Yang Y. et al., "Neuroprotection by delayed administration of topiratmate in rat model of middle cerebral artery embolization", Brain Research, vol. 804, No. 2, 1998, pp. 169-176, XP000921218.
York, DA et al, "Effects of Topirament on High Fat Diet-Induced Obesity", FASEB journal, Fed. of America Soc. for Experimental Biology, Bethesda, MD, US., vol. 14, No. 4, Apr. 2000. p. A431, XP000915192.
Young, WB et al, "Topiramate: a case series study in migraine prophylaxis" Cephalalgia (2002), (22)659-663.
Ziegler. E., et al.:"Zur Reaktivitat von C=Ndoppelbindungssytemen, VI. Reaktionen mit Sulfonamiden und Sulfamiden". Zeitschrift Fur Naturforschung, vol. 30B, 1975, pp. 951-953, XP008067475.
Alcaraz et al., Org. Lett., 2004, 6(16), pp. 2705-2708.
Beaudoin et al., J. Org. Chem., 2003, 68, pp. 115-119.
Birch et al., J. Med. Chem., 1999, 42, pp. 3342-3355.
Delgado et al., Tet Lett, 1988, 29(3), pp. 3671-3676.
Estave et al., Tet Lett, 2002, 43, pp. 1019-1021.
Gavernet et al., Bioorg & Med Chem., 2007, 15, pp. 5604-4516.
Hedayatullah et al., Phosphorus and Sulfur, 1985, 25(1), pp. 33-38.
Hirayama et al., Bioorg & Med Chem., 2002, 10, pp. 1509-1523.
Kim et al., Tet Lett, 23(14), pp. 1505-1508, 1982.
Kubicki et al., J Mol Struct., 2001, 531(1-3), p. 65-70.
Lee et al., Org. Chem 1990 55(25) pp. 6098-6104.
Muniz et al., SYNLETT, 2005, 1, pp. 149-151.
Nelson et al., J. Med. Chem., 1977, 20(7), pp. 880-885.
Nelson et al., J. Med. Chem., 1979, 22(9), pp. 1125-1127.
Nicolaou et al., Chem. Eur. J., 2004, 10, pp. 5581-5606.
Okada et al., Tet Lett, 2000, 41, pp. 7047-7051.
Park et al., J. Med. Chem., 2002, 45, pp. 5295-5302.
Winum et al., Org. Lett., 2001, 3(14), pp. 2241-2243.
Xu et al., SYNLETT, 2004, 11, pp. 1901-1904.
Zhong et al., J. Comb. Chem., 2004, 6, pp. 556-563.
Chemische Berichte 1959 92 pp. 509-513 (See English translation provided).
Behl et al., Endocrinology, vol. 138, No. 1, pp. 101-106, 1997.
Coyle et al., Science, vol. 262, Issue 5134, pp. 689-695, 1993.
Desagher et al., The Journal of Neuroscience, 1996, 16(8), pp. 2553-2562.
Tabner et al., The Journal of Biological Chemistry, vol. 280, No. 43, pp. 35789-35792, Oct. 28, 2005.
Taylor et al., Science, vol. 296, pp. 1991-1995 (2002).
New England Journal of Medicine, vol. 342:505-507, 2001.
Merck Manuals Online Medical Library, www.merck.com, 2007.
Cleeves et al., "Trazodone is ineffective in essential tremor", J. Neurol Nerusurg Psychiatry, 1990, 53:268-269.
Koller et al., "Essential Tremor Variants: Effect of Treatment", abstract, Clinical Pharmacology, 1987.
Robinson et al. "Pregablin not Effective for Essential Tremor", www.medpagetoday.com, 2009.
Handley and Mithani, Naunyn. Schmied. Arch. Pharmacol., 327, 1-5, 1984.
Aron et al., Neuropharmacology, 10, 459-469, 1971.
Meert et al., Pharmacol. Biochem. Behav.; 2005, 80(2), pp. 309-326.
MacDonald et al., CNS Drugs, 2002, 16(8): 549-562.
Walden et al., Neuropsychobiology, 1998,38: 181-84.
Byrn et al., Pharmaceutical Research, Kluwer Academic Publishers, New York, NY, US, vol. 12, No. 7, 1995, pp. 945-954.
Bernando, L., Prevention of epilepsy after head trauma: do we need drugs or a new approach?, 2003, Epilepsia, 44, (Suppl. 10), 27-33.
D'Ambrosio et al., Curr. Opin. Neurol. Dec. 2004; 17(6): 731-735.
Jones et al. "Screening for Major Depression in Epilepsy with Common Self-Report Depression Inventories", Epilepsia, May 2005; 46(5):731-735.
Kane et al., Psychopharmacological Bulletin, vol. 24, pp. 62-67 (1988).
Kaplan & Sadock's Comprehensive Textbook of Psychiatry, Seventh Edition, vol. II, Lippincott Williams & Wilkins: Philadelphia, pp. 2467-2468, 2000.
Kaplan & Sadock's Comprehensive Textbook of Psychiatry, Seventh Edition, vol. II, Lippincott Williams & Wilkins: Philadelphia, pp. 2470-2471, 2000.
Physician's Desk Reference; Kaplan & Sadock's Comprehensive Textbook of Psychiatry, Seventh Edition, vol. II, Lippincott Williams & Wilkins: Philadelphia, pp. 2466-2467, 2000 (olanzapine).
Physician's Desk Reference; Kaplan & Sadock's Comprehensive Textbook of Psychiatry, Seventh Edition, vol. II, Lippincott Williams & Wilkins: Philadelphia, pp. 2456-2463, 2000 (clozapine).
Physician's Desk Reference; Kaplan & Sadock's Comprehensive Textbook of Psychiatry, Seventh Edition, vol. II, Lippincott Williams & Wilkins: Philadelphia, pp. 2463-2466, 2000 (risperidone).
Physician's Desk Reference; Kaplan & Sadock's Comprehensive Textbook of Psychiatry, Seventh Edition, vol. II, Lippincott Williams & Wilkins: Philadelphia, pp. 2469-2470, 2000 (quetiapine).
Harwood, AJ, Molecular Psychiatry (2005) 10,117-126.
Goodman and Gilman's The Pharmacological Basis of Therapeutics, Eleventh Edition, McGraw Hill, Hypnotics and Sedatives, Chapter 16, pp. 401-427 (2006).

Goodman and Gilman's The Pharmacological Basis of Therapeutics, Eleventh Edition, McGraw Hill, Hypnotics and Sedatives, Chapter 17, pp. 429-459 (2006).
Goodman and Gilman's The Pharmacological Basis of Therapeutics, Eleventh Edition, McGraw Hill, Hypnotics and Sedatives, Chapter 19, pp. 429-459 (2006).
Sullivan, P., Epilepsy & Behavior 7 (2005) S12-S17.
Brodie, M.S.; Pesold, C; Appel, S.B. Alcohol Clin Exp Res 1999, 23, pp. 1848-1852.
Edeh et al, (1987) Relationship between interictal psychopathology and the type of epilepsy. Results of a survey in general practice. Br J Psychiatry 151:95-101.
Ettinger et al., (2004) Depression and comorbidity in community-based patients with epilepsy or asthma. Neurology 63:1008-1014.
Forsgren et al., (1990) An incident case-referent study of epileptic seizures in adults. Epilepsy Res 6:66-81.
Hesdorffer et al. (2006) Depression and suicide attempt as risk factors for incident unprovoked seizures. Ann Neurol 59:35-41.
Hesdorffer et al. (2000) Major depression is a risk factor for seizures in older adults. Ann Neurol 47:246-249.
Jacoby et al. (1996) The clinical course of epilepsy and its psychosocial correlates: findings from a U.K. Community study. Epilepsia 37:148-161.
Kanner, AM., (2006) Epilepsy, suicidal behaviour, and depression: do they share common pathogenic mechanisms? Lancet Neurol 5:107-108.
Krampfl et al., The European Journal of Neuroscience; vol. 22, Issue: 1, pp. 10-20, 2005.
Ottman et al., Epilepsia, 52(2):308-315, 2011.
Scimemi et al., The Journal of Neuroscience: the official journal of Society for Neuroscience; vol. 25; Issue: 43, pp. 10016-10024, 2005.
Wise RA, Drug Alcohol Depend, 1998, 51, pp. 13-22.
Wise RA, NIDA Res Mono, 1984, 50, pp. 15-33.
Dib, Jean G., Current Medical Research and Opinion, 2004, 20, 12, p. 1857-1861.
Thienel et al., Acta Neurologica Scandinavica, 2004, 110, 4, p. 221-231.
Brandt et al., Neuropsychobiology, 1998, 38, pp. 202 to 203.
Tanimukai et al., International Pharmacopsychiatry, 1970, vol. 5, No. 1, pp. 35 to 43.
Office Action mailed Mar. 26, 2008 in U.S. Appl. No. 11/154,443.
Notice of Allowance mailed Dec. 31, 2008 in U.S. Appl. No. 11/154,443.
Notice of Allowance mailed Jun. 8, 2009 in U.S. Appl. No. 11/154,443.
Notice of Allowance mailed Oct. 9, 2009 in U.S. Appl. No. 11/154,443.
Notice of Allowance dated Feb. 9, 2010 in U.S. Appl. No. 11/154,443.
Notice of Allowance dated May 25, 2010 in U.S. Appl. No. 11/154,443.
Notice of Allowance dated Sep. 20, 2010 in U.S. Appl. No. 11/154,443.
Notice of Allowance dated Jan. 25, 2011 in U.S. Appl. No. 11/154,443.
Notice of Allowance dated May 4, 2011 in U.S. Appl. No. 11/154,443.
Notice of Allowance dated Aug. 12, 2011 in U.S. Appl. No. 11/154,443.
Office Action mailed Oct. 3, 2007 in U.S. Appl. No. 11/154,386.
Office Action mailed Jul. 9, 2008 in U.S. Appl. No. 11/154,386.
Notice of Allowance mailed Mar. 6, 2009 in U.S. Appl. No. 11/154,386.
Notice of Allowance mailed Sep. 10, 2009 in U.S. Appl. No. 11/154,386.
Notice of Allowance dated Feb. 23, 2010 in U.S. Appl. No. 11/154,386.
Notice of Allowance dated Oct. 22, 2010 in U.S. Appl. No. 11/154,386.
Notice of Allowance dated Jul. 19, 2012 in U.S. Appl. No. 11/154,386.
Office Action mailed Apr. 14, 2008 in U.S. Appl. No. 11/209,122.
Notice of Allowance mailed Oct. 30, 2008 in U.S. Appl. No. 11/209,122.
Office Action mailed Mar. 20, 2009 in U.S. Appl. No. 11/209,122.
Notice of Allowance mailed Sep. 24, 2009 in U.S. Appl. No. 11/209,122.
Notice of Allowance mailed Jan. 13, 2010 in U.S. Appl. No. 11/209,122.
Notice of Allowance mailed Jan. 11, 2011 in U.S. Appl. No. 11/209,122.
Notice of Allowance mailed Jun. 1, 2011 in U.S. Appl. No. 11/209,122.
Notice of Allowance mailed Oct. 18, 2011 in U.S. Appl. No. 11/209,122.
Notice of Allowance dated Mar. 20, 2012 in U.S. Appl. No. 11/209,122.
Office Action mailed Sep. 10, 2008 in U.S. Appl. No. 11/406,794.
Notice of Allowance dated Mar. 13, 2009 in U.S. Appl. No. 11/406,794.
Notice of Allowance dated Jul. 17, 2009 in U.S. Appl. No. 11/406,794.
Office Action mailed Nov. 2, 2009 in U.S. Appl. No. 11/406,794.
Notice of Allowance dated Mar. 17, 2010 in U.S. Appl. No. 11/406,794.
Notice of Allowance dated Jul. 1, 2010 in U.S. Appl. No. 11/406,794.
Notice of Allowance dated Nov. 29, 2010 in U.S. Appl. No. 11/406,794.
Notice of Allowance dated Mar. 14, 2011 in U.S. Appl. No. 11/406,794.
Notice of Allowance dated Jun. 30, 2011 in U.S. Appl. No. 11/406,794.
Corrected Notice of Allowance dated Jul. 20, 2011 in U.S. Appl. No. 11/406,794.
Notice of Allowance dated Oct. 4, 2011 in U.S. Appl. No. 11/406,794.
Notice of Allowance dated Jan. 17, 2012 in U.S. Appl. No. 11/406,794.
Notice of Allowance dated May 10, 2012 in U.S. Appl. No. 11/406,794.
Office Action mailed May 2, 2008 in U.S. Appl. No. 11/611,961.
Final Office Action mailed Jan. 29, 2009 in U.S. Appl. No. 11/611,961.
Notice of Allowance dated Jun. 2, 2009 in U.S. Appl. No. 11/611,961.
Notice of Allowance dated Jan. 6, 2010 in U.S. Appl. No. 11/611,961.
Notice of Allowance dated Apr. 30, 2010 in U.S. Appl. No. 11/611,961.
Notice of Allowance dated Aug. 12, 2010 in U.S. Appl. No. 11/611,961.
Notice of Allowance dated Nov. 30, 2010 in U.S. Appl. No. 11/611,961.
Notice of Allowance dated Mar. 14, 2011 in U.S. Appl. No. 11/611,961.
Notice of Allowance dated Jul. 18, 2011 in U.S. Appl. No. 11/611,961.
Notice of Allowance dated Oct. 26, 2011 in U.S. Appl. No. 11/611,961.
Notice of Allowance dated Feb. 6, 2012 in U.S. Appl. No. 11/611,961.
Notice of Allowance dated May 23, 2012 in U.S. Appl. No. 11/611,961.
Office Action mailed Nov. 26, 2008 in U.S. Appl. No. 11/612,071.
Final Office Action mailed Jun. 8, 2009 in U.S. Appl. No. 11/612,071.
Notice of Allowance mailed Oct. 11, 2011 in U.S. Appl. No. 11/612,071.
Notice of Allowance mailed Mar. 9, 2012 in U.S. Appl. No. 11/612,071.
Final Office Action mailed Aug. 5, 2008 in U.S. Appl. No. 11/612,146.
Final Office Action mailed Oct. 29, 2009 in U.S. Appl. No. 11/612,146.
Notice of Allowance mailed Apr. 25, 2012 in U.S. Appl. No. 11/612,146.
Office Action mailed Jan. 29, 2009 in U.S. Appl. No. 11/612,174.
Office Action mailed Jul. 11, 2011 in U.S. Appl. No. 12/431,141.

Final Office Action mailed Dec. 15, 2011 in U.S. Appl. No. 12/431,141.
Interview Summary dated Mar. 26, 2012 in U.S. Appl. No. 12/431,141.
Office Action mailed Mar. 30, 2009 in U.S. Appl. No. 11/612,202.
Office Action mailed Jan. 14, 2010 in U.S. Appl. No. 11/612,202.
Notice of Allowance mailed Jul. 29, 2010 in U.S. Appl. No. 11/612,202.
Notice of Allowance mailed Nov. 15, 2010 in U.S. Appl. No. 11/612,202.
Notice of Allowance mailed Mar. 4, 2011 in U.S. Appl. No. 11/612,202.
Notice of Allowance dated Sep. 19, 2011 in U.S. Appl. No. 11/612,202.
Notice of Allowance mailed Jan. 4, 2012 in U.S. Appl. No. 11/612,202.
Notice of Allowance mailed Apr. 16, 2012 in U.S. Appl. No. 11/612,202.
Office Action mailed Jul. 9, 2010 in U.S. Appl. No. 11/612,222.
Office Action mailed Apr. 12, 2011 in U.S. Appl. No. 11/612,222.
Final Office Action mailed Oct. 4, 2011 in U.S. Appl. No. 11/612,222.
Office Action mailed Jul. 21, 2009 in U.S. Appl. No. 11/612,249.
Final Office Action mailed Jan. 28, 2010 in U.S. Appl. No. 11/612,249.
Office Action mailed Oct. 15, 2010 in U.S. Appl. No. 11/612,249.
Office Action mailed Apr. 22, 2011 in U.S. Appl. No. 11/612,249.
Office Action mailed Oct. 6, 2011 in U.S. Appl. No. 10/612,249.
Office Action mailed May 21, 2008 in U.S. Appl. No. 11/674,021.
Final Office Action mailed Jul. 31, 2009 in U.S. Appl. No. 11/674,021.
Notice of Allowance mailed Jun. 16, 2010 in U.S. Appl. No. 11/674,021.
Notice of Allowance mailed Dec. 15, 2010 in U.S. Appl. No. 11/674,021.
Notice of Allowance dated Aug. 22, 2011 in U.S. Appl. No. 11/674,021.
Notice of Allowance dated May 11, 2012 in U.S. Appl. No. 13/301,109.
Office Action mailed Apr. 29, 2009 in U.S. Appl. No. 11/750,600.
Final Office Action mailed Dec. 16, 2009 in U.S. Appl. No. 11/750,600.
Final Office Action mailed Mar. 11, 2010 in U.S. Appl. No. 11/750,600.
Notice of Allowance mailed May 28, 2010 in U.S. Appl. No. 11/750,600.
Notice of Allowance mailed Dec. 15, 2010 in U.S. Appl. No. 11/750,600.
Office Action/Interview Summary dated Sep. 1, 2011 in U.S. Appl. No. 11/750,600.
Notice of Allowance dated Sep. 12, 2011 in U.S. Appl. No. 11/750,600.
Notice of Allowance mailed Dec. 22, 2011 in U.S. Appl. No. 11/750,600.
Office Action dated Mar. 30, 2012 in U.S. Appl. No. 11/750,600.
Office Action mailed Jun. 24, 2009 in U.S. Appl. No. 12/055,433.
Final Office Action mailed Feb. 23, 2010 in U.S. Appl. No. 12/055,433.
Office Action mailed Sep. 22, 2010 in U.S. Appl. No. 12/055,433.
Office Action mailed Jun. 8, 2011 in U.S. Appl. No. 12/055,433.
Office Action mailed Dec. 22, 2011 in U.S. Appl. No. 12/055,433.
Interview Summary dated Apr. 4, 2012 in U.S. Appl. No. 12/055,433.
Office Action mailed May 26, 2011 in U.S. Appl. No. 12/055,695.
Office Action mailed Jul. 15, 2011 in U.S. Appl. No. 12/055,695.
Final Office Action mailed Nov. 21, 2011 in U.S. Appl. No. 12/055,695.
Office Action mailed Nov. 15, 2010 in U.S. Appl. No. 12/055,924.
Notice of Allowance mailed Apr. 12, 2011 in U.S. Appl. No. 12/055,924.
Office Action mailed Oct. 6, 2011 in U.S. Appl. No. 12/349,184.
Notice of Allowance dated May 11, 2012 in U.S. Appl. No. 12/349,184.
Office Action mailed Jun. 1, 2010 in U.S. Appl. No. 12/488,079.
Notice of Allowance mailed Dec. 14, 2010 in U.S. Appl. No. 12/488,079.
Notice of Allowance mailed Jun. 21, 2011 in U.S. Appl. No. 12/488,079.
Notice of Allowance dated Nov. 1, 2011 in U.S. Appl. No. 12/488,079.
Notice of Allowance dated Mar. 1, 2012 in U.S. Appl. No. 12/488,079.
Notice of Allowance dated Jun. 18, 2012 in U.S. Appl. No. 12/488,079.
Office Action mailed Jul. 8, 2011 in U.S. Appl. No. 12/502,472.
Notice of Allowance mailed Nov. 28, 2011 in U.S. Appl. No. 12/502,472.
Notice of Allowance dated Mar. 28, 1012 in U.S. Appl. No. 12/502,472.
Notice of Allowance dated Jul. 16, 1012 in U.S. Appl. No. 12/502,472.
O'Donnell et al., Chapter 15, "Drug Therapy of Depression and Anxiety Disorders", Goodman & Gilman's The Pharmacological Basis of Therapeutics, $12^{th}$ Edition, 2011, pp. 397-415.
McNamara, J., Chapter 21, "Pharmacotherapy of the Epilepsies", Goodman & Gilman's The Pharmacological Basis of Therapeutics, $12^{th}$ Edition, 2011, pp. 583-607.
Benjamin et al. J Biomol Screening, 2006, vol. 11, pp. 29-39.
Brown et al. Tetrahedron, 1987, vol. 43, pp. 4071-4078.
Dunham et al. J Am Pharm Assoc Sci Ed, 1957, vol. 46, pp. 208-209.
Ettinger et al. Neurotherapeutics, 2007, vol. 4, pp. 75-83.
Gavernet et al. Bioorg Med Chem 2007, vol. 15, pp. 1556-1567.
Gavernet et al. J Med Chem, 2009, vol. 52, pp. 1592-1601.
Gribkoff, V., Expert Opin Ther Pat., 2003 vol. 7, pp737-748.
Keck et al., J. Clin. Psychiatry, 2002, 63 (suppl 4).
Kohling, R., Epilepsia, 2002, vol. 43, pp. 1278-1295.
Kuzimski et al., Epilepsia, 2005, vol. 46, pp. 481-489.
Landmark, C., CNS Drugs, 2008, vol. 22, pp. 27-47.
Liu et al., Epilepsy Res, 2006, vol. 70, pp. 263-268.
Liu et al., Neuropharmacology, 2003, vol. 44, pp. 413-422.
Lombardo et al., Mol Brain Res, 1996, vol. 35, pp. 84-90.
Lothman et al., Epilepsy Res, 1988, vol. 2, pp. 356-366.
Lothman et al., Epilepsy Res, 1988, vol. 2, pp. 367-379.
Lukyanetz et al., Epilepsia, 2002, vol. 43, pp. 9-18.
Maryanoff et al, Drugs Future, 1989, vol. 14, pp. 342-344.
Maryanoff et al, J Med Chem, 2008, vol. 51, pp. 2518-2521.
Maryanoff et al., Curr Top Med Chem, 2009, vol. 9, pp. 1049-1062.
Maryanoff, B., J Med Chem, 2009, vol. 52, pp. 3431-3440.
Orloff et al., Proc Soc Exp Biol Med, 1949, vol. 70, pp. 254-257.
Parker et al., J Med Chem, 2009, vol. 52, pp. 7528-7536.
Remington's the Science and Practice of Pharmacy, 19th Edition, Published 1998, vol. I, pp. 371-375.
Rogawski et al., Nat Med, 2004, vol. 10, pp. 685-692.
Rogawski, M., Epilepsy Res, 2006, vol. 69, pp. 273-294.
Shank et al., CNS Neurosci Ther, 2008, vol. 14, pp. 120-142.
Shank et al., Epilepsia, 1994, vol. 35, pp. 450-460.
Shank et al., J Enzym Inh Med Chem, 2008, vol. 23, pp. 271-276.
Shingles et al., Anal Biochem, 1997, vol. 252, pp. 190-197.
Soderpalm, B., Eur J Pain, 2002, vol. 6, Suppl A, p. 3-9.
Stella et al., Drugs, 29: 455-473 (1985).
Swinyard et al., J Pharmacol Exp Ther, 1952, vol. 106, pp. 319-330.
Swinyard, E., Epilepsia, 1969, vol. 10, pp. 107-119.
Wang et al., Science, 1998 vol. 282, pp. 1890-1893.
White et al., Antiepileptic Drugs, 5th Ed., 2002, pp. 36-48.
White et al., Epilepsy Res, 1992, vol. 12, pp. 217-226.
White et al., Int Rev Neurobiol, 2007, vol. 81, pp. 85-110.
Winum et al., Expert Opin Ther Pat, 2006, vol. 16, pp. 27-47.
Zaremba et al., Pharmacol Rep, 2006, vol. 58, pp. 1-12.

* cited by examiner

USE OF BENZO-FUSED HETEROCYCLE SULFAMIDE DERIVATIVES FOR THE TREATMENT OF OBESITY

This application claims the benefit of U.S. Provisional Application 60/751,499, filed on Dec. 19, 2005, which is incorporated by reference herein in its entirety.

FIELD OF THE INVENTION

The present invention is directed to the use of benzo-fused heterocycle sulfamide derivatives for the treatment of obesity, for promoting weight loss and/or for suppressing appetite.

BACKGROUND OF THE INVENTION

Obesity is a state of excess adipose tissue mass. Although often viewed as equivalent to increased body weight, this need not be the case-lean but very muscular individuals may be overweight by arbitrary standards without having increased adiposity. Body weights are distributed continuously in populations, so that a medically meaningful distinction between lean and obese is somewhat arbitrary. Obesity is therefore more effectively defined by assessing its linkage to morbidity or mortality.

Although not a direct measure of adiposity, the most widely used method to gauge obesity is the body mass index (BMI), which is equal to weight/height$^2$ (in kg/m$^2$). Other approaches to quantifying obesity include anthropometry (skin-fold thickness), densitometry (underwater weighing), computed tomography (CT) or magnetic resonance imaging (MRI), and electrical impedance. Using data from the Metropolitan Life Tables, BMIs for the midpoint of all heights and frames among both men and women range from 19 to 26 kg/m$^2$; at a similar BMI, women have more body fat than men. Based on unequivocal data of substantial morbidity, a BMI of 30 is most commonly used as a threshold for obesity in both men and women. Large-scale epidemiologic studies suggest that all-cause, metabolic, and cardiovascular morbidity begin to rise (albeit at a slow rate) when BMIs are ≧25, suggesting that the cut-off for obesity should be lowered. Some authorities use the term overweight (rather than obese) to describe individuals with BMIs between 25 or 27 and 30. A BMI between 25 and 30 should be viewed as medically significant and worthy of therapeutic intervention, especially in the presence of risk factors that are influenced by adiposity, such as hypertension and glucose intolerance.

Recent data from the National Health and Nutrition Examination Surveys (NHANES) show that the percent of the American adult population with obesity (BMI>30) has increased from 14.5% (between 1976 and 1980) to 22.5% (between 1998 and 1994). As many as 50% of U.S. adults ≧20 years of age were overweight (defined as BMI>25) between the years of 1998 and 1991. Because substantial health risks exist in many individuals with BMI between 25 and 30, the increasing prevalence of medically significant obesity raises great concern. Obesity is more common among women and in the poor; the prevalence in children is also rising at a worrisome rate.

Obesity has major adverse effects on health. Morbidly obese individuals (>200% ideal body weight) have as much as a twelve-fold increase in mortality. Morality rates rise as obesity increases, particularly when obesity is associated with increased intraabdominal fat (see above). It is also apparent that the degree to which obesity affects particular organ systems is influenced by susceptibility genes that vary in the population. Obese individuals have a 50-100% increased risk of premature death from all causes compared to individuals with normal body weight. Over 300,000 deaths a year in the United States may be attributable to obesity.

There remains a need to provide an effective treatment for obesity.

SUMMARY OF THE INVENTION

The present invention is directed to a method for the treatment of obesity, for promoting weight loss and/or for suppressing appetite comprising administering to a subject in need thereof a therapeutically effective amount of a compound of formula (I)

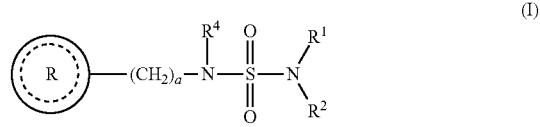

wherein

R$^1$ and R$^2$ are each independently selected from the group consisting of hydrogen and lower alkyl;

R$^4$ is selected from the group consisting of hydrogen and lower alkyl;

a is an integer from 1 to 2;

is selected from the group consisting of

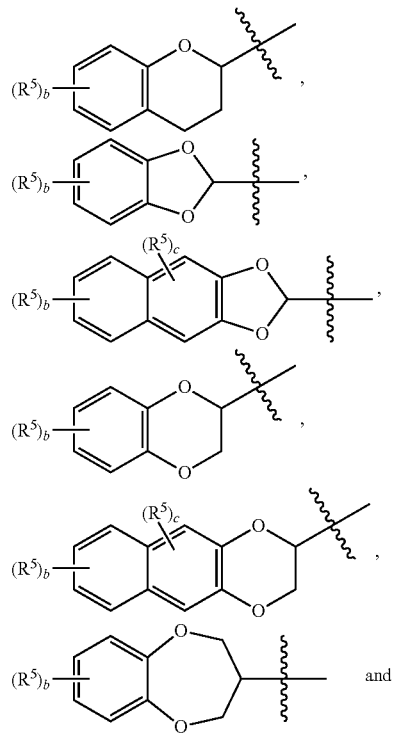

and

-continued

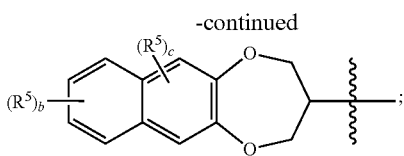

wherein b is an integer from 0 to 4; and wherein c is an integer from 0 to 2;

each $R^5$ is independently selected from the group consisting of halogen, lower alkyl and nitro;

provided that when

is

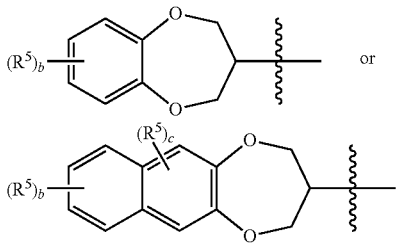

then a is 1;

or a pharmaceutically acceptable salt thereof.

The present invention is further directed to a method for the treatment of obesity, for weight loss and/or for suppressing appetite comprising administering to a subject in need thereof a therapeutically effective amount of compound of formula (II)

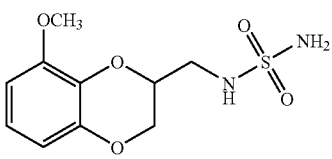
(II)

or a pharmaceutically acceptable salt thereof.

The present invention is further directed to a method for treating obesity, promoting weight loss and/or suppressing appetite comprising co-therapy with a therapeutically effective amount of at least one weight loss promoting agent and/or at least one appetite suppressing agent and a compound of formula (I) or formula (II) as described herein. In an embodiment, the present invention is directed to a method for treating obesity and/or promoting weight loss comprising co-therapy with at least one weight loss promoting agent and a compound of formula (I) as described here, preferably Compound #8 as described herein.

Exemplifying the invention is a method of treating obesity comprising administering to a subject in need thereof a therapeutically effective amount of any of the compounds described above. In another example, the invention is directed to a method of promoting weight loss comprising administering to a subject in need thereof a therapeutically effective amount of any of the compounds described above. In another example, the invention is directed to a method of suppressing appetite comprising administering to a subject in need thereof a therapeutically effective amount of any of the compounds described above. Further exemplifying the invention is a method for delaying gastic emptying comprising administering to a subject in need thereof a therapeutically effective amount of any of the compound described herein.

DETAILED DESCRIPTION OF THE INVENTION

The present invention is directed to a method for the treatment of obesity, for promoting weight loss and/or suppressing appetite comprising administering to a subject in need thereof a therapeutically effective amount of a compound of formula (I)

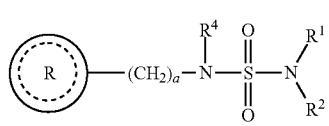
(I)

or a pharmaceutically acceptable salt thereof, wherein

a, $R^1$, $R^2$ and $R^4$ are as herein defined. The present invention is further directed to a method for delaying gastic emptying comprising administering to a subject in need thereof a therapeutically effective amount of any of the compounds described herein.

The present invention is further directed to the treatment of obesity comprising administering to a subject in need thereof, co-therapy with a therapeutically effective amount of at least one weight loss promoting agent and/or at least one appetite suppressing agent and a compound of formula (I) or formula (II) as described herein.

In one embodiment of the present invention the present invention is directed to a methods for the treatment of obesity comprising administering to a subject in need thereof a therapeutically effective amount compounds of formula (I) or (II) as previously described or their pharmaceutical salts wherein the weight lost is fat and in a more preferred embodiment is white adipose tissue.

In one embodiment of the present invention the present invention is directed to a methods for promoting weight loss comprising administering to a subject in need of or desiring to loss weight a therapeutically effective amount compounds of formula (I) or (II) as previously described or their pharmaceutical salts wherein the weight lost is fat and in a more preferred embodiment is white adipose tissue.

As used herein, the term "obesity" shall be defined as a body mass index (BMI) of greater than or equal to about 25, preferably a BMI of greater than or equal to about 30. Thus as used herein, the term "obesity" shall include both overweight and clinically obese subjects/patients.

As used herein, the term "weight loss promoting agent" shall mean any pharmaceutical agent which promotes weight loss. Suitable examples include, but are not limited to rimonabant, orlistat, sibutramine, mazindol, benzphetamine, phenmetrazine, phentermine, diethylpropion, mazindol, phenylpropanolamine, ephedrine, quipazine, fluoxetine, sertraline, fenfluramine, dexfenfluramine, apomorphine, Exendin, dehydroepiandrosterone, etiocholandione, testosterone, oxandrolone, topiramate, and the like. Preferably, the weight loss promoting agent is rimonabant, topiramate, orlistat or sibutramine. Similarly, as used herein, the term "appetite suppressing agent" shall mean any pharmaceutical agent or natural product which suppresses appetite which include, but are not limited to, appetite-suppressants acting through adrenergic mechanisms such as benzphetamine, phenmetrazine, phentermine, diethylpropion, mazindol, sibutramine, phenyl-propanolamine or, ephedrine; appetite-suppressant agents acting through serotonergic mechanisms such as quipazine, fluoxetine, sertraline, fenfluramine, or dexfenfluramine; appetite-suppressant agents acting through dopamine mechanisms, eg, apomorphine; appetite-suppressant agents acting through histaminergic mechanisms (eg, histamine mimetics, H3 receptor modulators); enhancers of energy expenditure such as beta-3 adrenergic agonists and stimulators of uncoupling protein function; leptin and leptin mimetics; neuropeptide Y antagonists; melanocortin-1, 3 and 4 receptor modulators; cholecystokinin agonists; glucagon-like peptide-1 (GLP-1) mimetics and analogues (eg, Exendin); androgens (eg, dehydroepiandrosterone and derivatives such as etiocholandione), testosterone, anabolic steroids (eg, oxandrolone), and steroidal hormones; galanin receptor antagonists; cytokine agents such as ciliary neurotrophic factor; amylase inhibitors; enterostatin agonists/mimetics; orexin/hypocretin antagonists; urocortin antagonists; bombesin agonists; modulators of protein kinase A; corticotropin-releasing factor mimetics; cocaine- and amphetamine-regulated transcript mimetics; calcitonin-gene related peptide mimetics; and fatty acid synthase inhibitors.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Wherein the present invention is directed to co-therapy or combination therapy, comprising administration of one or more compound(s) of formula (I) or formula (II) and one or more weight loss promoting agent and/or at least one appetite suppressing agent, "therapeutically effective amount" shall mean that amount of the combination of agents taken together so that the combined effect elicits the desired biological or medicinal response. For example, the therapeutically effective amount of co-therapy comprising administration of a compound of formula (I) or formula (II) and at least one weight loss promoting agent and/or at least one appetite suppressing agent would be the amount of the compound of formula (I) or formula (II) and the amount of the weight loss promoting agent and/or at least one appetite suppressing agent that when taken together or sequentially have a combined effect that is therapeutically effective. Further, it will be recognized by one skilled in the art that in the case of co-therapy with a therapeutically effective amount, as in the example above, the amount of the compound of formula (I) or formula (II) and/or the amount of the weight loss promoting agent and/or at least one appetite suppressing agent individually may or may not be therapeutically effective.

As used herein, the terms "co-therapy" and "combination therapy" shall mean treatment of a subject in need thereof by administering one or more compounds of formula (I) or formula (II) in combination with one or more weight loss promoting agent and/or the appetite suppressing agent, wherein the compound(s) of formula (I) or formula (II) and the weight loss promoting agent and/or the appetite suppressing agent are administered by any suitable means, simultaneously, sequentially, separately or in a single pharmaceutical formulation. Where the compound(s) of formula (I) or formula (II) and the weight loss promoting agent and/or the appetite suppressing agent are administered in separate dosage forms, the number of dosages administered per day for each compound may be the same or different. The compound(s) of formula (I) or formula (II) and the weight loss promoting agent" and/or the appetite suppressing agent may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The compound(s) of formula (I) or formula (II) and the weight loss promoting agent and/or the appetite suppressing agent (s) may be administered according to simultaneous or alternating regimens, at the same or different times during the course of the therapy, concurrently in divided or single forms.

In an embodiment of the present invention $R^1$ is selected from the group consisting of hydrogen and methyl. In another embodiment of the present invention $R^2$ is selected from the group consisting of hydrogen and methyl. In yet another embodiment of the present invention $R^1$ and $R^2$ are each hydrogen or $R^1$ and $R^2$ are each methyl.

In an embodiment of the present invention —$(CH_2)_a$— is selected from the group consisting of —$CH_2$— and —$CH_2$—$CH_2$—. In another embodiment of the present invention —$(CH_2)_a$— is —$CH_2$—.

In an embodiment of the present $R^4$ is selected from the group consisting of hydrogen and methyl, preferably, $R^4$ is hydrogen.

In an embodiment of the present invention a is 1.

In an embodiment of the present invention b is an integer from 0 to 2. In another embodiment of the present invention c is an integer from 0 to 2. In another embodiment of the present invention b is an integer from 0 to 1. In another embodiment of the present invention c is an integer from 0 to 1. In yet another embodiment of the present invention the sum of b and c is an integer form 0 to 2, preferably an integer form 0 to 1. In yet another embodiment of the present invention b is an integer from 0 to 2 and c is 0.

In an embodiment of the present invention,

is selected from the group consisting of

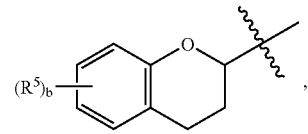

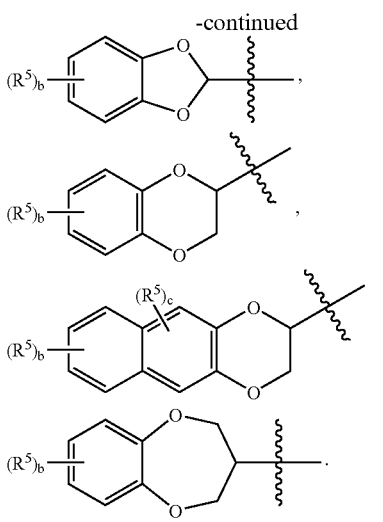

In another embodiment of the present invention,

is selected from the group consisting of

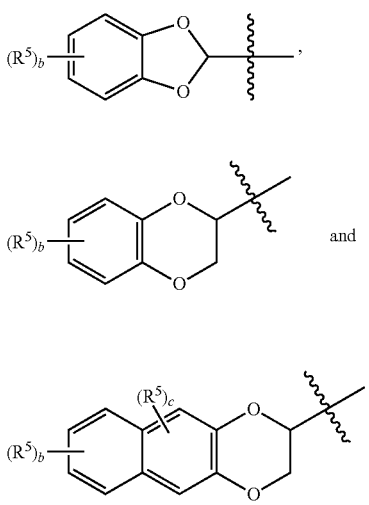

In an embodiment of the present invention,

is selected from the group consisting of 2-(2,3-dihydro-benzo[1,4]dioxinyl), 2-(benzo[1,3]dioxolyl), 3-(3,4-dihydro-benzo[1,4]dioxepinyl), 2-(6-chloro-2,3-dihydro-benzo[1,4]dioxinyl), 2-(6-fluoro-2,3-dihydro-benzo[1,4]dioxinyl), 2-(chromanyl), 2-(5-fluoro-2,3-dihydro-benzo[1,4]dioxinyl), 2-(7-chloro-2,3-dihydro-benzo[1,4]dioxinyl), 2-(6-chloro-benzo[1,3]dioxolyl), 2-(7-nitro-2,3-dihydro-benzo[1,4]dioxinyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), 2-(8-chloro-2,3-dihydro-benzo[1,4]dioxinyl), 2-(2,3-dihydro-naphtho[2,3-b][1,4]dioxinyl) and 2-(4-methyl-benzo[1,3]dioxolyl).

In another embodiment of the present invention,

is selected from the group consisting 2-(benzo[1,3]dioxolyl), 2-(2,3-dihydro-benzo[1,4]dioxinyl), 2-(6-chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl). In another embodiment of the present invention

is selected from the group consisting of 2-(2,3-dihydro-benzo[1,4]dioxinyl), 2-(7-methyl-2,3-dihydro-benzo[1,4]dioxinyl) and 2-(6-bromo-2,3-dihydro-benzo[1,4]dioxinyl).

In an embodiment of the present invention $R^5$ is selected from the group consisting of halogen and lower alkyl. In another embodiment of the present invention $R^5$ is selected from chloro, fluoro, bromo and methyl.

In an embodiment of the present invention, the stereo-center on the compound of formula (I) is in the S-configuration. In another embodiment of the present invention, the stereo-center on the compound of formula (I) is in the R-configuration.

In an embodiment of the present invention the compound of formula (I) is present as an enantiomerically enriched mixture, wherein the % enantiomeric enrichment (% ee) is greater than about 75%, preferably greater than about 90%, more preferably greater than about 95%, most preferably greater than about 98%.

Additional embodiments of the present invention, include those wherein the substituents selected for one or more of the variables defined herein (i.e. $R^1$, $R^3$, $R^4$, X—Y and A) are independently selected to be any individual substituent or any subset of substituents selected from the complete list as defined herein.

Representative compounds of the present invention, are as listed in Tables 1 below. Additional compounds of the present invention are as listed in Table 3. In Tables 1 and 2 below, the column headed "stereo" defines the stereo-configuration at the carbon atom of the heterocycle attached at the starred bond. Where no designation is listed, the compound was prepared as a mixture of stereo-configurations. Where an "R" or "S" designation is listed, the stereo-configuration was based on the enantiomerically enriched starting material.

TABLE 1

Representative Compounds of Formula (I)

| ID No. | R | Stereo | $(CH_2)_a$ | $NR^4$ | $R^1$ | $R^2$ |
|---|---|---|---|---|---|---|
| 1 | 2-(2,3-dihydro-benzo[1,4]dioxinyl) | | $CH_2$ | NH | H | H |
| 2 | 2-(benzo[1,3]dioxolyl) | | $CH_2$ | NH | H | H |
| 3 | 3-(3,4-dihydro-2H-benzo[1,4]dioxepinyl) | | $CH_2$ | NH | H | H |
| 4 | 2-(2,3-dihydro-benzo[1,4]dioxinyl) | S | $CH_2$ | NH | H | H |
| 5 | 2-(2,3-dihydro-benzo[1,4]dioxinyl) | R | $CH_2$ | NH | H | H |
| 6 | 2-(2,3-dihydro-benzo[1,4]dioxinyl) | | $CH_2$ | NH | methyl | methyl |
| 7 | 2-(2,3-dihydro-benzo[1,4]dioxinyl) | | $CH_2$ | $N(CH_3)$ | H | H |
| 8 | 2-(6-chloro-2,3-dihydrobenzo[1,4]dioxinyl) | S | $CH_2$ | NH | H | H |
| 9 | 2-(6-fluoro-2,3-dihydrobenzo[1,4]dioxinyl) | S | $CH_2$ | NH | H | H |
| 10 | 2-(chromanyl) | | $CH_2$ | NH | H | H |
| 13 | 2-(5-fluoro-2,3-dihydrobenzo[1,4]dioxinyl) | S | $CH_2$ | NH | H | H |
| 14 | 2-(7-chloro-2,3-dihydrobenzo[1,4]dioxinyl) | S | $CH_2$ | NH | H | H |
| 15 | 2-(6-chloro-benzo[1,3]dioxolyl) | | $CH_2$ | NH | H | H |
| 16 | 2-(2,3-dihydro-benzo[1,4]dioxinyl) | | $CH_2CH_2$ | NH | H | H |
| 18 | 2-(7-nitro-2,3-dihydro-benzo[1,4]dioxinyl) | S | $CH_2$ | NH | H | H |
| 19 | 2-(7-methyl-2,3-dihydrobenzo[1,4]dioxinyl) | S | $CH_2$ | NH | H | H |
| 20 | 2-(5-chloro-2,3-dihydrobenzo[1,4]dioxinyl) | S | $CH_2$ | NH | H | H |
| 22 | 2-(8-methoxy-2,3-dihydrobenzo[1,4]dioxinyl) | S | $CH_2$ | NH | H | H |
| 24 | 2-(6-bromo-2,3-dihydrobenzo[1,4]dioxinyl) | S | $CH_2$ | NH | H | H |
| 29 | 2-(6,7-dichloro-2,3-dihydrobenzo[1,4]dioxinyl) | S | $CH_2$ | NH | H | H |
| 30 | 2-(8-chloro-2,3-dihydrobenzo[1,4]dioxinyl) | S | $CH_2$ | NH | H | H |
| 33 | 2-(2,3-dihydro-naphtho[2,3-b][1,4]dioxinyl) | S | $CH_2$ | NH | H | H |
| 35 | 2-(4-methyl-benzo[1,3]dioxolyl) | | $CH_2$ | NH | H | H |

TABLE 2

Additional Compounds of the Present Invention

| ID No. | Y | Stereo | X | $NR^{14}$ | $R^{11}$ | $R^{12}$ |
|---|---|---|---|---|---|---|
| 23 | 2-(5-methoxy-2,3-dihydrobenzo[1,4]dioxinyl) | S | $CH_2$ | NH | H | H |
| 26 | 2-(6-methylcarbonyl-2,3-dihydrobenzo[1,4]dioxinyl) | S | $CH_2$ | NH | H | H |
| 32 | 2-(6-methoxycarbonyl-2,3-dihydrobenzo[1,4]dioxinyl) | S | $CH_2$ | NH | H | H |
| 34 | 2-(6-hydroxymethyl-2,3-dihydrobenzo[1,4]dioxinyl) | S | $CH_2$ | NH | H | H |
| 36 | 2-(7-amino-2,3-dihydrobenzo[1,4]dioxinyl) | S | $CH_2$ | NH | H | H |

As used herein, unless otherwise noted, "halogen" shall mean chlorine, bromine, fluorine and iodine.

As used herein, unless otherwise noted, the term "alkyl" whether used alone or as part of a substituent group, includes straight and branched chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, the notation "*" shall denote the presence of a stereogenic center.

When a particular group is "substituted" (e.g., alkyl, aryl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenyl-alkyl-amino-carbonyl-alkyl" substituent refers to a group of the formula Abbreviations used in the specification, particularly the Schemes and Examples, are as follows

| | |
|---|---|
| DCC = | Dicyclohexyl Carbodiimide |
| DCE = | Dichloroethane |
| DCM = | Dichloromethane |
| DIPEA or DIEA = | Diisopropylethylamine |
| DMF = | N,N-Dimethylformamide |
| DMSO = | Dimethylsulfoxide |
| EDC = | Ethylcarbodiimide |
| Et$_3$N or TEA = | Triethylamine |
| Et$_2$O = | Diethyl ether |
| EA or EtOAc = | Ethyl acetate |
| EtOH = | Ethanol |
| IPA = | 2-propanol |
| Hept = | Heptane |
| HOBT = | 1-Hydroxybenzotriazole |
| HPLC = | High Pressure Liquid Chromatography |
| LAH = | Lithium Aluminum Hydride |
| M or MeOH = | Methanol |
| NMR = | Nuclear Magnetic Resonance |
| Pd—C = | Palladium on Carbon Catalyst |
| RP HPLC = | Reverse Phase High Pressure Liquid Chromatography |
| RT or rt = | Room temperature |
| TEA | Triethylamine |
| TFA = | Trifluoroacetic Acid |
| THF = | Tetrahydrofuran |
| TLC = | Thin Layer Chromatography |

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (I) may be prepared according to the process outlined in Scheme 1.

Scheme 1

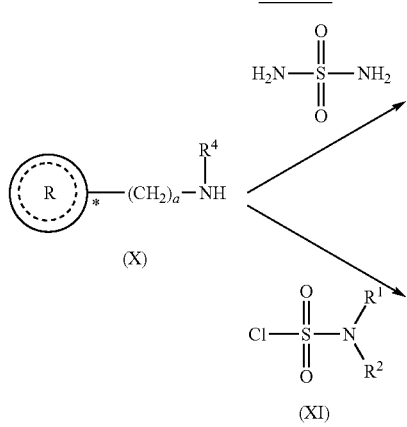

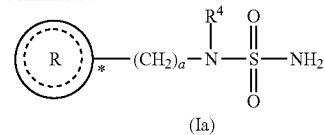

(Ia)

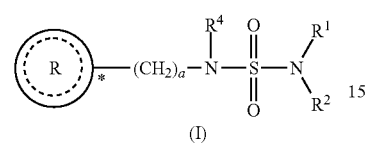

(I)

Accordingly, a suitably substituted compound of formula (X), a known compound or compound prepared by known methods, is reacted with sulfamide, a known compound, preferably wherein the sulfamide is present in an amount in the range of about 2 to about 5 equivalents, in an organic solvent such as THF, dioxane, and the like, preferably at an elevated temperature in the range of about 50° C. to about 100° C., more preferably at about reflux temperature, to yield the corresponding compound of formula (Ia).

Alternatively, a suitably substituted compound of formula (X), a known compound or compound prepared by known methods, is reacted with a suitably substituted compound of formula (XI), a known compound or compound prepared by known methods, in the presence of a base such as TEA, DIPEA, pyridine, and the like, in an organic solvent such as DMF, DMSO, and the like, to yield the corresponding compound of formula (I).

Compounds of formula (X) wherein

is

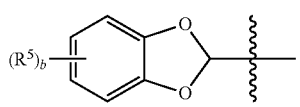

may be prepared according to the process outlined in Scheme 2.

Scheme 2

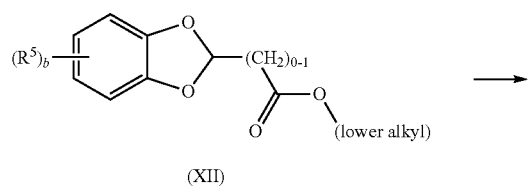

(XII)

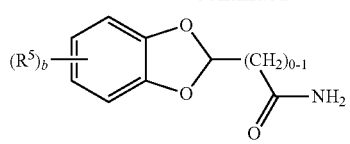

(XIII)

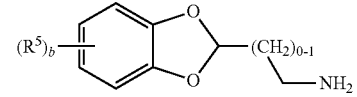

(Xa)

Accordingly, a suitably substituted compound of formula (XII), a known compound or compound prepared by known method (for example as described in Scheme 3 above) is reacted with $NH_4OH$, a known compound, optionally in an organic solvent such as acetonitrile, and the like, to yield the corresponding compound of formula (XIII).

The compound of formula (XIII) is reacted with a suitably selected reducing agent, such as LAH, and the like, in an organic solvent such as THF, diethyl ether, and the like, to yield the corresponding compound of formula (Xa).

Compounds of formula (X) wherein

is selected from

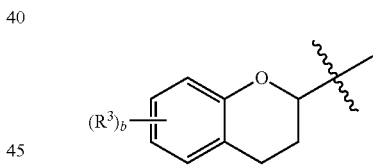

may be prepared according to the process outlined in Scheme 3.

Scheme 3

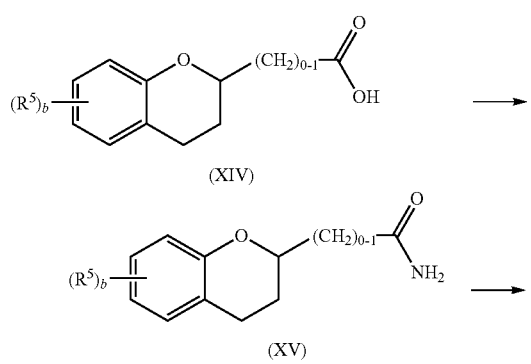

(XIV)

(XV)

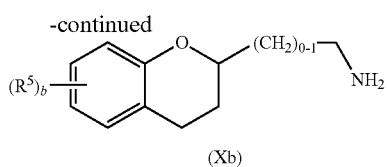

(Xb)

Accordingly, a suitably substituted compound of formula (XIV), a known compound or compound prepared by known methods, is reacted with $NH_4OH$, in the presence of a coupling agent such as DCC, and the like, optionally in an organic solvent such as acetonitrile, and the like, to yield the corresponding compound of formula (XV).

The compound of formula (XV) is reacted with a suitably selected reducing agent, such as LAH, and the like, in an organic solvent such as THF, diethyl ether, and the like, to yield the corresponding compound of formula (Xb).

Compounds of formula (X) wherein

is selected from

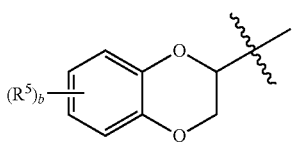

and wherein a is 2, may be prepared according to the process outlined in Scheme 4.

Scheme 5

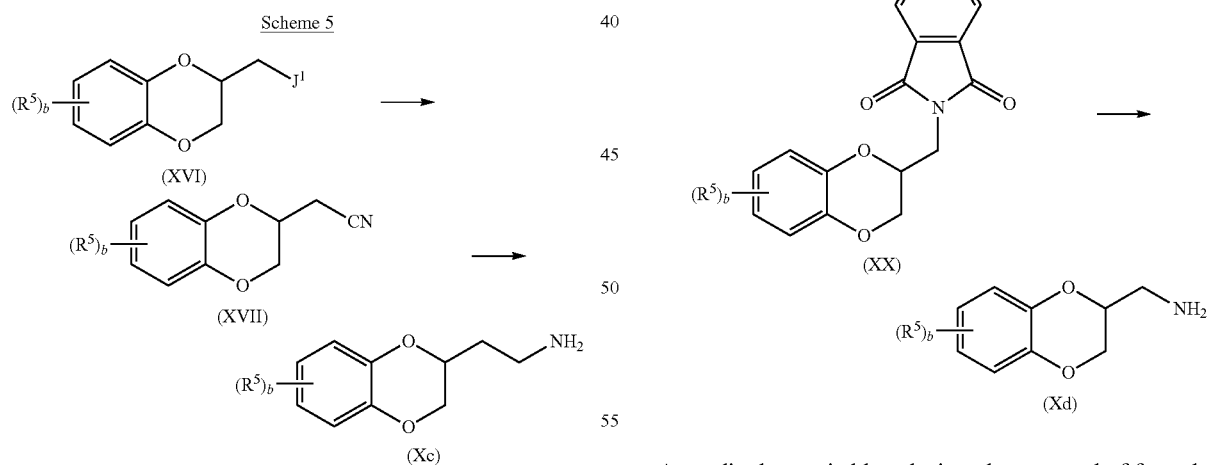

Accordingly, a suitably substituted compound of formula (XVI) wherein $J^1$ is a suitable leaving group such as Br, Cl, I, tosyl, mesyl, triflyl, and the like, a known compound or compound prepared by known methods (for example, by activating the corresponding compound wherein $J^1$ is OH), is reacted with a cyanide such as potassium cyanide, sodium cyanide, and the like, in an organic solvent such as DMSO, DMF, THF, and the like, to yield the corresponding compound of formula (XVII).

The compound of formula (XVII) is reduced according to known methods, for example by reacting with a suitable reducing agent such as LAH, borane, and the like, to yield the corresponding compound of formula (Xc).

Compounds of formula (X) wherein

is selected from

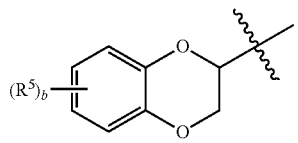

and wherein a is 1, may be prepared according to the process outlined in Scheme 5.

Scheme 5

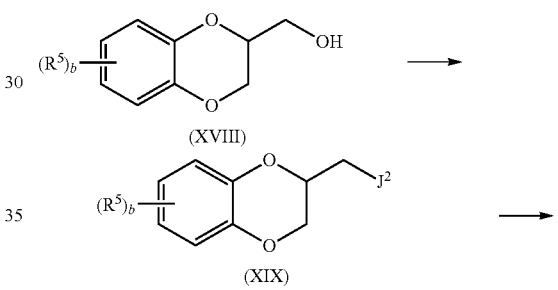

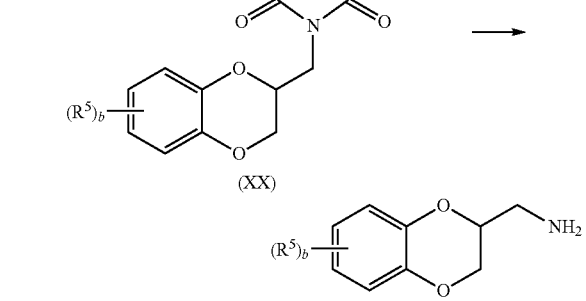

Accordingly, a suitably substituted compound of formula (XVIII), a known compound or compound prepared by known methods is activated, according to known method, to yield the corresponding compound of formula (XIX), wherein $J^2$ is a suitable leaving group, such tosylate, Cl, Br, I, mesylate, triflate, and the like.

The compound of formula (XIX) is reacted with a phthalimide salt such as potassium phthlimide, sodium phthalimide, and the like, in an organic solvent such as DMF, DMSO, acetonitrile, and the like, preferably, at an elevated temperature in the range of from 50° C. to about 200° C., more preferably, at about reflux temperature, to yield the corresponding compound of formula (XX).

The compound of formula (XX) is reacted with N₂H₄, a known compound, in an organic solvent such as ethanol, methanol, and the like, preferably, at an elevated temperature in the range of from about 50° C. to about 100° C., more preferably, at about reflux temperature, and the like, to yield the corresponding compound of formula (Xd).

One skilled in the art will recognize that compounds of formula (X) wherein

is selected from

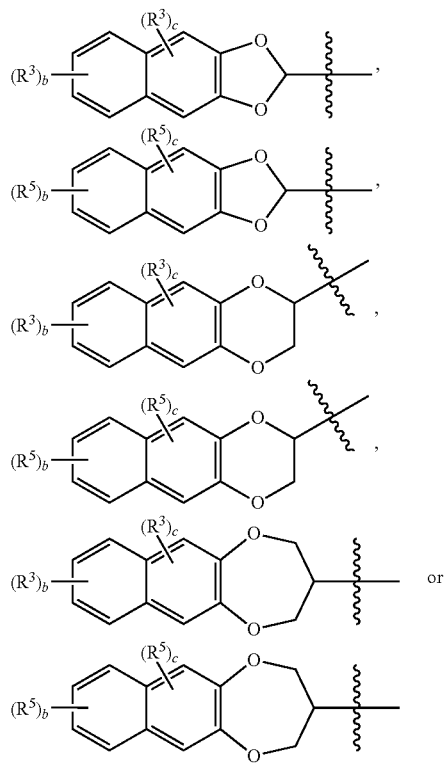

may be similarly prepared according to known methods or for example, according to the processes outlined in Schemes 2 through 5 above, by selecting and substituting the corresponding naphthyl-fused compounds for the benzo-fused starting materials.

One skilled in the art will further recognize that wherein a single enantiomer (or a mixture of enantiomers wherein one enantiomer is enriched) of a compound of formula (X) is desired, the above processes as described in Schemes 1 through 5 may be applied by substituting the corresponding single enantiomer (or mixture of enantiomers wherein one enantiomer is enriched) for the appropriate starting material.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg and may be given at a dosage of from about 0.01-200.0 mg/kg/day, preferably from about 0.1 to 100 mg/kg/day, more preferably from about 0.5-50 mg/kg/day, more preferably from about 1.0-25.0 mg/kg/day, more preferably from about 0.5-10.0 mg/kg/day, most preferably from about 1.0 to about 5.0 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating depression described in the present invention may also be carried out using a pharmaceutical composition comprising any of the compounds as defined herein and a pharmaceutically acceptable carrier. The pharmaceutical composition may contain between about 0.1 mg and 1000 mg, preferably about 50 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Compounds of this invention may be administered in any of the foregoing compositions and according to dosage regimens established in the art whenever treatment of depression is required.

The daily dosage of the products may be varied over a wide range from 0.01 to 150 mg/kg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 1500 mg/kg of body weight per day. Preferably, the range is from about 0.1 to about 100.0 mg/kg of body weight per day, more preferably, from about 0.5 mg/kg to about 50 mg/kg, more preferably, from about 1.0 to about 25.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

Example 1

((3,4-Dihydro-2H-benzo[b][1,4]dioxepin-3-yl)methyl)sulfamide (Compound #3)

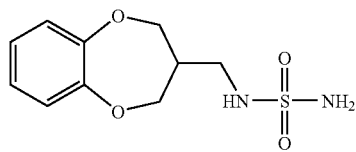 [SMILES: NS(=O)(=O)NCC1COc2ccccc2OC1]

Catechol (5.09 g, 46.2 mmol) and potassium carbonate were combined in acetonitrile and heated to reflux for one hour. 2-Chloromethyl-3-chloro-1-propene (5.78 g, 46.2 mmol) was added and the reaction was continued at reflux for 24 hours. The solution was cooled to room temperature and filtered. The filtrate was evaporated and the residue was diluted with water and extracted with diethyl ether (3×). The combined organic solution was dried over MgSO$_4$ and concentrated. Chromatography (2% ethyl ether in hexane) yielded 3-methylene-3,4-dihydro-2H-benzo[b][1,4]dioxepine as a colorless oil.

MS (ESI): 163.2 (M+H$^+$)

$^1$H NMR (300 MHz, CDCl$_3$), δ: 6.94 (m, 4H), 5.07 (s, 2H), 4.76 (s, 4H).

3-Methylene-3,4-dihydro-2H-benzo[b][1,4]dioxepine (5.00 g, 30.8 mmol) was dissolved in dry THF (100 mL). Borane-THF (1.0 M in THF, 10.3 mL) was added at 0° C. The reaction was stirred at RT for 5 hours. Aminosulfonic acid (6.97 g, 61.6 mmol) was added. The reaction was heated to reflux overnight. The reaction was cooled to room temperature and aqueous sodium hydroxide (3.0 M, 100 mL) was added. The solution was extracted with ethyl acetate (3×100 mL). The combined organic solution was dried over MgSO$_4$. The solution was concentrated under vacuum and purified by chromatography (2% to 8% methanol in dichloromethane) to yield ((3,4-dihydro-2H-benzo[b][1,4]dioxepin-3-yl)methyl) amine as a colorless oil.

MS (ESI): 180.1 (M+H$^+$)

$^1$H NMR (300 MHz, DMSO), δ: 6.92 (m, 4H), 4.21 (m, 2H), 4.07 (m, 2H), 3.33 (broad, 2H), 3.16 (d, J=4 Hz, 1H), 2.72 (d, J=4 Hz, 1H), 2.30 (m, 1H).

((3,4-Dihydro-2H-benzo[b][1,4]dioxepin-3-yl)methyl) amine (2.90 g, 16.2 mmol) and sulfamide (3.11 g, 32.4 mmol) were combined in dry dioxane (60 ml) and heated to reflux overnight. Chloroform was added and the precipitate was removed by filtration. The filtrate was concentrated under vacuum and purified by chromatography (2% to 8% acetone in dichloromethane) to yield the title compound as an off-white solid.

258.8 (M+H$^+$)

$^1$H NMR (300 MHz, DMSO), δ: 6.92 (m, 4H), 6.71 (broad, 1H), 6.59 (broad, 2H), 4.19 (m, 2H), 4.04 (m, 2H), 3.00 (m, 2H), 2.39 (m, 1H).

Example 2

N-(2,3-Dihydro-benzo[1.4]dioxin-2-ylmethyl)-sulfamide (Compound #1)

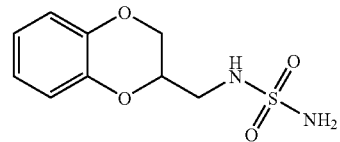 [SMILES: NS(=O)(=O)NCC1COc2ccccc2O1]

Racemic 2,3-dihydro-1,4-benzdioxin-2-ylmethylamine (4.4 g, 26 mmol) and sulfamide (5.1 g, 53 mmol) were combined in 1,4 dioxane (100 mL) and refluxed for 2 h. The reaction was cooled to room temperature and a small amount of solid was filtered and discarded. The filtrate was evaporated in vacuo and the residue was purified using flash column chromatography (DCM:Methanol—10:1) to yield a white solid. The solid was recrystallized from DCM to yield the title compound as a white solid.

mp: 97.5-98.5° C.

Elemental Analysis:

| Anal Calc: | C, 44.25; H, 4.95; N, 11.47; S, 13.13 |
|---|---|
| Anal Found: | C, 44.28; H, 4.66; N, 11.21; S, 13.15 |

H$^1$ NMR (DMSO d6) δ 6.85 (m, 4H), 6.68 (bd s, 3H, NH), 4.28 (m, 2H), 3.97 (dd, J=6.9, 11.4 Hz, 1H), 3.20 (m, 1H), 3.10 (m, 1H).

Example 3

(Benzo[1,3]-dioxol-2-ylmethyl)sulfamide (Compound #2)

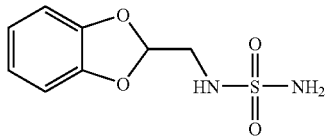 [SMILES: NS(=O)(=O)NCC1Oc2ccccc2O1]

Catechol (10.26 g, 93.2 mmol), sodium methoxide (25% by weight in methanol, 40.3 g, 186 mmol), and methyl dichloroacetate (13.3 g, 93.2 mmol) were combined in dry methanol (100 mL). The solution was heated to reflux overnight. The reaction was cooled to room temperature, acidified by addition of concentrated hydrochloric acid and then reduced in volume under vacuum to about 50 mL. Water was added and the mixture was extracted with diethyl ether (3×100 mL). The combined organic solution was dried with $MgSO_4$, concentrated to a brown solid, and chromatographed (2% ethyl acetate in hexane) to yield benzo[1,3]dioxole-2-carboxylic acid methyl ester as a colorless oil.

MS (ESI): 195.10 ($M+H^+$).

$^1$H NMR (300 MHz, $CDCl_3$), δ: 6.89 (broad, 4H), 6.29 (s, 1H), 4.34 (q, J=7 Hz, 2H), 1.33 (t, J=7 Hz, 3H).

To benzo[1,3]dioxole-2-carboxylic acid methyl ester (7.21 g, 40.0 mmol) was added ammonium hydroxide (29% in water, 10 mL) and enough acetonitrile to make the mixture homogeneous (~5 mL). The solution was stirred for two hours at room temperature and then distilled water was added. Benzo[1,3]dioxole-2-carboxylic acid amide precipitated as a white solid and was collected by filtration and used without further purification.

MS (ESI): 160.00 ($M+H^+$)

$^1$H NMR (300 MHz, DMSO), δ: 7.99 (s, broad, 1H), 7.72 (s, broad, 1H), 6.94 (m, 2H) 6.86 (m, 2H), 6.30 (s, 1H).

Benzo[1,3]dioxole-2-carboxylic acid amide (5.44 g, 32.9 mmol) was dissolved in tetrahydrofuran (THF, 100 mL). Lithium aluminum hydride (LAH, 1M in THF, 39.5 mL, 39.5 mmol) was added slowly to the solution at room temperature. The reaction was stirred at room temperature for 24 hours. Distilled water was added to destroy the excess LAH. Aqueous sodium hydroxide (3.0 M, 100 mL) was added and the solution was extracted with ethyl acetate (3×100 mL). The combined organic solution was washed with water and dried over $MgSO_4$. The solvent was evaporated to yield C-benzo[1,3]dioxol-2-yl-methylamine as a colorless oil.

MS (ESI): 152.1 ($M+H^+$)

$^1$H NMR (300 MHz, $CDCl_3$), δ: 6.87 (m, 4H), 6.09 (t, J=4 Hz, 1H), 3.13 (d, J=4 Hz, 2H)

C-Benzo[1,3]dioxol-2-yl-methylamine (2.94 g, 19.4 mmol) and sulfamide (3.74 g, 38.9 mmol) were combined in dry dioxane (50 mL) and the solution was heated to reflux overnight. The reaction was concentrated and the residue was chromatographed (2% to 10% acetone in dichloromethane) to yield the title compound as a white solid.

MS (ESI): 230.0 ($M+H^+$)

$^1$H NMR (300 MHz, $CDCl_3$), δ: 6.87 (m, 4H), 6.25 (t, J=4 Hz, 1H), 4.79 (broad, 1H), 4.62 (broad, 1H), 3.64 (d, J=4 Hz, 2H).

Example 4

(2S)-(−)-N-(2,3-Dihydro-benzo[1,4]dioxin-2-ylmethyl)-sulfamide (Compound #4)

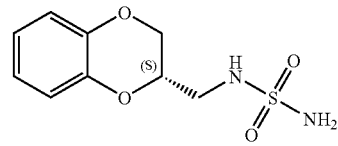

Catechol (13.2 g, 0.12 mol) and potassium carbonate (16.6 g, 0.12 mol) were stirred in DMF (250 mL) and (2R)-glycidyl tosylate (22.8 g, 0.10 mol) was added and the reaction was stirred at 60° C. for 24 h. The reaction was cooled to room temperature and diluted with ice water (1 L) and extracted with diethyl ether (4 times). The combined organic solution was washed 3 times with 10% potassium carbonate, once with water, once with brine and evaporated in vacuo to yield a white solid which was purified by flash column chromatography (DCM:Methanol—50:1) to yield ((2S)-2,3-dihydro-benzo[1,4]dioxin-2-yl)-methanol as a solid.

The solid (13.3 g, 68 mmol) was dissolved in pyridine (85 mL) cooled to 0° C., p-toluenesulfonyl chloride (13.0 g, 68 mmol) was added and the reaction mixture stirred at room temperature for 20 h. The reaction was diluted with diethyl ether (1 L) and 1N HCl (1.2 L). The organic layer was separated and washed 2 times with 1N HCl (500 mL), 4 times with water (150 mL), once with brine, dried ($MgSO_4$) and evaporated in vacuo to yield a white solid which was purified by flash column chromatography (Hept:EA—2:1) to yield toluene-4-sulfonic acid (2S)-2,3-dihydro-benzo[1,4]dioxin-2-ylmethyl ester as a white solid.

The white solid was combined with potassium phthalimide (14.4 g, 78 mmol) in DMF (250 mL) and heated to reflux for 1 h, cooled to room temperature and poured into vigorously stirring water (1.5 L) and stirred 30 min. White solid was filtered and the solid was washed several times with water, 2% NaOH, and water again and let air dry to yield a (2S)-2-(2,3-Dihydro-benzo[1,4]dioxin-2-ylmethyl)-isoindole-1,3-dione as white powdery solid.

The powdery white solid was combined with hydrazine (2.75 g, 86 mmol) in EtOH (225 mL) and heated at reflux for 2 h, cooled to room temperature and 1N HCl added to pH 1.0 and stirred for 15 min. White solid was filtered and washed with fresh EtOH (solid discarded) and the filtrate was evaporated in vacuo to a solid, which was partitioned between diethyl ether and dilute aqueous NaOH. The diethyl ether solution was dried ($Na_2SO_4$) and evaporated in vacuo to a yield a light yellow oil. The oil was purified by flash column chromatography (DCM:MeOH—10:1) to yield an oil. A portion of the oil (4.82 g, 29 mmol) in 2-propanol (250 mL) was treated with 1N HCl (30 mL) and heated on steambath until homogeneous and then let cool to room temperature. After 3 h, the mixture was ice cooled for 2 h. A white flaky solid (the corresponding HCl salt of (2S)-C-(2,3-Dihydro-benzo[1,4]dioxin-2-yl)-methylamine) was filtered off and then recrystallized again from 2-propanol to yield a white solid.

$[α]_D$=−69.6 (c=1.06, EtOH)

The white solid was partitioned between DCM and dilute NaOH, and the DCM was dried (NaSO₄) and evaporated in vacuo to yield (2S)-C-(2,3-Dihydro-benzo[1,4]dioxin-2-yl)-methylamine as an oil.

$[\alpha]_D = -57.8$ (c=1.40, CHCl₃)

The oil (2.1 g, 12.7 mmol) and sulfamide (2.44 g, 25.4 mmol) were refluxed in dioxane (75 mL) for 2 h and the crude product was purified by flash column chromatography (DCM:MeOH 10:1) to yield a white solid, which was recrystallized from DCM to yield the title compound as a white crystalline solid.

mp 102-103° C.

$[\alpha]_D = -45.1°$ (c=1.05, M);

¹H NMR (DMSO-d6) δ 6.86 (m, 4H), 6.81 (bd s, 3H, NH), 4.3 (m, 2H), 3.97 (dd, J=6.9, 11.4 Hz, 1H), 3.20 (dd, J=5.5, 13.7 Hz, 1H), 3.10 (dd, J=6.9, 13.7 Hz, 1H)

Elemental Analysis:

| Anal Calc: | C, 44.25; H, 4.95; N, 11.47; S, 13.13 |
|---|---|
| Anal Found: | C, 44.20; H, 4.69; N, 11.40; S, 13.22. |

Example 5

N-(2,3-Dihydro-benzo[1,4]dioxin-2-ylmethyl)-N',N'dimethylsulfamide (Compound #6)

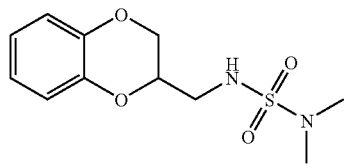 [SMILES: CN(C)S(=O)(=O)NCC1COc2ccccc2O1]

Racemic 2,3-dihydro-1,4-benzdioxin-2-ylmethylamine (8.25 g, 5.0 mmol) and triethylamine (1.52 g, 15 mmol) were combined in DMF (10 mL) and cooled in an ice bath as dimethylsulfamoyl chloride (1.44 g, 10 mmol) was added. The reaction mixture was then stirred for 3 hr with continued cooling. The reaction mixture was partitioned between ethyl acetate and water, and the ethyl acetate solution was washed with brine, dried (MgSO₄) and evaporated in vacuo to yield an oil. The oil was purified using flash column chromatography (ethyl acetate:Heptane—1:1) to yield a white solid, which was recrystallized (ethyl acetate/Hexane) to yield the title compound as a white floccular solid.

mp 76-78° C.

MS 273 (MH⁺)

Elemental Analysis:

| Anal Calc: | C, 48.52; H, 5.92; N, 10.29; S, 11.78 |
|---|---|
| Anal Found: | C, 48.63; H, 5.62; N, 10.20; S, 11.90 |

¹H NMR (CDCl₃) δ 6.87 (m, 4H), 4.59 (bd m, 1H, NH), 4.35 (m, 1H), 4.27 (dd, J=2.3, 11.4 Hz, 1H), 4.04 (dd, J=7.0, 11.4, 1H), 3.36 (m, 2H), 2.82 (s, 6H).

Example 6

N-(2,3-Dihydro-benzo[1,4]dioxin-2-ylmethyl)-N-methylsulfamide (Compound #7)

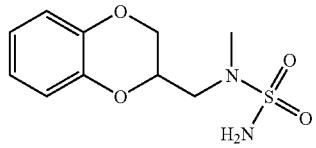 [SMILES: CN(CC1COc2ccccc2O1)S(N)(=O)=O]

Racemic 2,3-dihydro-1,4-benzdioxin-2-ylmethylamine (825 mg, 5 mmol) was dissolved in ethyl formate (15 mL), refluxed for 30 min and evaporated in vacuo to yield N-(2,3-dihydro-benzo[1,4]dioxin-2-ylmethyl)-formamide as an oil.

The oil in diethyl ether (25 mL) was treated with 1M LAH in THF (9.0 mL, 9.0 mmol) at 0° C. and stirred for 5 h at room temperature. The reaction was cooled in an ice bath and quenched with water (0.50 mL), followed by 3 N NaOH (0.50 mL) and water (0.50 mL). The mixture was then stirred at room temperature for 1 h. Solid was filtered and the filtrate was evaporated in vacuo to yield a residue which was partitioned between 1N HCl and diethyl ether. The aqueous phase was basified with 1N NaOH and extracted with diethyl ether. The organic phase was dried (MgSO₄) and evaporated in vacuo to yield (2,3-dihydro-benzo[1,4]dioxin-2-ylmethyl)-methyl-amine as an oil.

MS 180 (MH⁺)

¹H NMR (CDCl₃) δ 6.85 (m, 4H), 4.30 (m, 2H), 4.02 (dd, J=7.9, 11.6 Hz, 1H), 2.85 (m, 2H), 2.50 (s, 3H)

The oil (380 mg, 2.1 mmol) and sulfamide (820 mg, 8.5 mmol) were combined in dioxane (15 mL), refluxed for 1.5 h and evaporated in vacuo to yield a crude residue. The residue was purified via column chromatography (ethyl acetate/Heptane 1:1) and the resultant solid was recrystallized from ethyl acetate/Hexane to yield the title compound as a white solid.

mp 97-98° C.

MS 257 (M⁻¹)

Elemental Analysis:

| Anal Calc: | C, 46.50; H, 5.46; N, 10.85; S, 12.41 |
|---|---|
| Anal Found: | C, 46.48; H, 5.65; N, 10.90; S, 12.07 |

¹H NMR (CDCl₃) δ 6.86 (m, 4H), 4.52 (bs, 2H), 4.46 (m, 1H), 4.29 (dd, J=2.3, 11.5 Hz, 1H), 4.05 (dd, J=6.5, 11.5 Hz, 1H), 3.51 (dd, J=6.7, 14.9 Hz, 1H), 3.40 (dd, J=5.9, 14.9 Hz, 1H), 2.99 (s, 3H).

Example 7

(2S)-(−)-N-(6-Chloro-2,3-dihydro-benzo[1,4]dioxin-2-ylmethyl)-sulfamide (Compound #8)

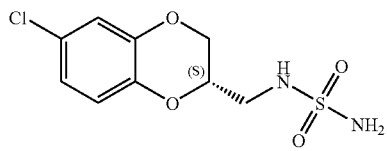

Following the procedure outlined in Example 4 above, 4-chlorocatechol was reacted to yield a mixture of (2S)-C-(7-Chloro-2,3-dihydro-benzo[1,4]dioxin-2-yl)-methylamine and (2S)-C-(6-Chloro-2,3-dihydro-benzo[1,4]dioxin-2-yl)-methylamine (ca. 3:1 ratio of 6-chloro:7-chloro isomers by RP HPLC).

The mixture was dissolved in 2-propanol (100 mL) and 1N HCl in diethyl ether was added until pH=1.0 was attained. The hydrochloride salt that precipitated was filtered (2.65 g) and re-crystallized from methanol/IPA to yield white crystals. The white crystals were partitioned between DCM and dilute NaOH. The DCM was dried and evaporated in vacuo to yield purified (2S)-C-(6-Chloro-2,3-dihydro-benzo[1,4]dioxin-2-yl)-methylamine as an oil.

$[\alpha]_D = -67.8$ (c=1.51, $CHCl_3$)

The oil (7.75 mmol) and sulfamide (1.50 g, 15.5 mmol) were combined in dioxane (50 mL) and refluxed for 2.0 h, cooled to room temperature and evaporated in vacuo to yield a solid. The product was purified via flash column using DCM/methanol 20:1 to yield the title compound as a white solid.

MS 277 ($M^{-1}$)

$[\alpha]_D = -59.9°$ (c=1.11, M)

$^1$H NMR ($CDCl_3$) δ 6.90 (d, J=2.2 Hz, 1H), 6.81 (m, 2H), 4.76 (m, 1H), 4.55 (s, 2H), 4.40 (m, 1H), 4.29 (dd, J=2.4, 11.5 Hz, 1H), 4.05 (dd, J=7.1, 11.5 Hz, 1H), 3.45 (m, 2H)

Elemental Analysis:

| Anal Calc: | C, 38.78; H, 3.98; N, 10.05 |
| Anal Found: | C, 38.80; H, 3.67; N, 9.99. |

The filtrates of the crystallized hydrochloride salt of (2S)-C-(6-Chloro-2,3-dihydro-benzo[1,4]dioxin-2-yl)-methylamine prepared above were recovered (ca. 1:1 of 6-chloro:7-chloro isomers) and evaporated in vacuo to yield a solid, which was partitioned between DCM (200 mL) and dilute NaOH (0.5 M, 50 mL). The DCM solution was washed once with brine, dried ($Na_2SO_4$) and evaporated in vacuo to yield an oil, which was purified via reverse phase HPLC (10-50% ACN with 0.16% TFA in water with 0.20% TFA) to yield (2S)-C-(7-Chloro-2,3-dihydro-benzo[1,4]dioxin-2-yl)-methylamine as a residue.

The residue was combined with sulfamide (0.90 g, 9.4 mmol) in dioxane (25 mL) and refluxed for 2.5 h, cooled to room temperature and evaporated in vacuo to yield an oil. The oil was purified by flash column chromatography using DCM/methanol—10:1 to yield (2S)-(−)-N-(7-Chloro-2,3-dihydro-benzo[1,4]dioxin-2-ylmethyl)-sulfamide as a white solid.

MS 277 ($M^{-1}$)

$^1$H NMR ($CDCl_3/CD_3OD$) δ 6.88 (d, J=0.7 Hz, 1H), 6.81 (m, 2H), 4.37 (m, 1H), 4.30 (dd, J=2.3, 11.6 Hz, 1H), 4.04 (dd, J=7.0, 11.6 Hz, 1H), 3.38 (m, 2H).

Example 8

Chroman-2-ylmethylsulfamide (Compound #10)

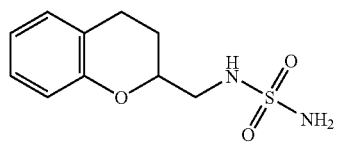 [SMILES: NS(=O)(=O)NCC1CCc2ccccc2O1]

Chroman-2-carboxylic acid (4.5 g, 25 mmol) and HOBT (3.86 g, 25 mmol) were combined in DCM (40 mL) and DMF (10 mL). Dimethylaminopropyl ethylcarbodiimide (EDC, 4.84 g, 25 mmol) was added at room temperature and the reaction mixture was stirred for 30 min. Ammonium hydroxide (2.26 mL, 33.4 mmol) was added and the reaction mixture was stirred for 16 h. The reaction mixture was diluted with DCM (50 mL) and water (50 mL) and the pH of the mixture was adjusted to about pH=3.0 with 1N HCl. The DCM was separated and the aqueous phase extracted twice with DCM. The combined DCM phase was dried ($Na_2SO_4$) and evaporated in vacuo to yield an oil, which was purified with flash column chromatography (ethyl acetate) to yield an oil.

The oil (5.35 g, 30 mmol) in THF (90 mL) was stirred as 1M LAH in THF (36 mL, 36 mmol) was added and the reaction mixture was then stirred at room temperature for 20 h. The reaction was quenched with water, stirred for 2 hours, the solution decanted, dried ($Na_2SO_4$) and evaporated in vacuo to yield C-chroman-2-yl-methylamine as an oily amine.

The oily amine (1.63 g, 10 mmol) and sulfamide (1.92 g, 20 mmol) were combined in dioxane (50 mL) and brought to reflux for 2 h. The solution was cooled and evaporated in vacuo to yield an oil, which was purified via column chromatography (DCM:Methanol 10:1) to yield a white solid. The solid was recrystallized from ethyl acetate/hexane to yield chroman-2-ylmethylsulfamide as a white solid.

mp 100-101° C.

MS 241 ($M^{-1}$)

Elemental Analysis:

| Anal Calc: | C, 49.57; H, 5.82; N, 11.56; S, 13.23 |
| Anal Found: | C, 49.57; H, 5.80; N, 11.75; S, 13.33. |

Example 9

2-(2,3-Dihydro-benzo[1,4]dioxin-2-yl)-ethylsulfamide (Compound #16)

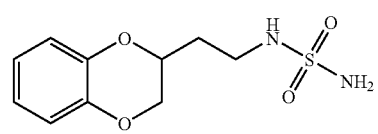 [SMILES: NS(=O)(=O)NCCC1COc2ccccc2O1]

Potassium cyanide (2.05 g, 31.5 mmol) was added to 2-bromomethyl-(2,3 dihydrobenzo[1,4]dioxine) (6.87 g, 30 mmol) in DMSO (90 mL) and stirred at ambient temperature for 20 h. The reaction mixture was then diluted with water (250 mL) and extracted twice with diethyl ether. The diethyl ether was washed with water, then washed twice with brine, dried ($Na_2SO_4$) and evaporated in vacuo to yield 2-cyanomethyl-(2,3 dihydrobenzo[1,4]dioxine) as a white solid.

$^1$H NMR ($CDCl_3$) δ 6.89 (m, 4H), 4.50 (m, 1H), 4.31 (dd, J=2.3, 11.5 Hz, 1H), 4.08 (dd, J=6.2, 11.6 Hz, 1H), 2.78 (d, J=6.1, Hz, 2H)

The 2-cyanomethyl-(2,3 dihydrobenzo[1,4]dioxine) was dissolved in THF (50 mL) and 1M BH₃ in THF (80 mL, 80 mmol) was added and the reaction mixture refluxed for 5 h, then stirred at ambient temperature for 16 h. With ice bath cooling, 2N HCl was added until pH=1.0 was achieved. The reaction mixture was then stirred for 1 h at room temperature and evaporated in vacuo to yield an oil. The oil was partitioned between 3N NaOH and diethyl ether, and the diethyl ether solution was washed with brine, dried (Na₂SO₄) and evaporated in vacuo to yield crude 2-(2,3 dihydrobenzo[1,4]dioxin-2-yl)ethylamine.

MS (M+H)⁺ 180.

The crude 2-(2,3 dihydrobenzo[1,4]dioxin-2-yl)ethylamine in dioxane (100 mL) was combined with sulfamide (3.0 g, 31 mmol) and heated to reflux for 2 h. The solution was cooled and evaporated in vacuo to yield an orange solid, which was purified by column chromatography (DCM:MeOH—10:1) to yield a white solid. The solid was re-crystallized from DCM to yield the title compound as a solid.

MS (M−1) 257
MP 101-103° C. (corr)
¹H NMR (CDCl₃): δ6.86 (m, 4H), 4.70 (m, 1H), 4.52 (s, 2H), 4.30 (m, 2H), 3.94 (dd, J=7.4, 11.3 Hz, 1H), 3.43 (dd, J=6.4, 12.9 Hz, 2H), 1.94 (dd, J=6.5, 12.9, 2H).
Elemental Analysis:

| Measured: | C, 46.48; H, 5.60; N, 10.81; S, 12.41 |
| Calculated: | C, 46.50; H, 5.46; N, 10.85; S, 12.41 |

Example 10

(2S)-(−)-N-(6,7 Dichloro-2,3-dihydro-benzo[1,4]dioxin-2-ylmethyl)-sulfamide (Compound #29)

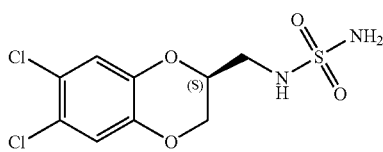

4,5 Dichloroatechol (8.6 g, 48 mmol) and potassium carbonate (6.64 g, 48 mmol) were stirred in DMF (200 mL). (2R)-Glycidyl tosylate (9.12 g, 40 mmol) was added and the reaction mixture was stirred at 60° C. for 24 h. The reaction mixture was cooled to room temperature and then diluted with ice water (600 mL) and extracted with diethyl ether (4 times). The combined organic solution was washed 3 times with 10% potassium carbonate, twice with brine, dried (MgSO₄) and evaporated in vacuo to yield a viscous oil of (2S)-2-(6,7-dichloro-2,3-dihydro-benzo[1,4]dioxine) methanol.

The (2S)-2-(6,7 dichloro-2,3-dihydro-benzo[1,4]dioxine) methanol oil (6.4 g, 27 mmol) was dissolved in pyridine (50 mL) cooled to 0° C. Then, p-toluenesulfonyl chloride (5.2 g, 27 mmol) was added and the reaction mixture was stirred at room temperature for 20 h. The reaction mixture was diluted with diethyl ether and 1N HCl (750 mL) and the organic layer was separated and washed 2 times with 1N HCl (250 mL), once with water (150 mL), twice with brine, dried (MgSO₄) and evaporated in vacuo to yield light yellow solid of toluene-4-sulfonic acid (2S)-6,7-dichloro-2,3-dihydro-benzo[1,4]dioxin-2-ylmethyl ester.

¹H NMR (CDCl3): δ 7.79 (d, J=8.3 Hz, 2H), 7.36 (d, J=8.0 Hz, 2H), 6.94 (s, 1H), 6.83 (s, 1H), 4.37 (m, 1H), 4.2 (m, 3H), 4.03 (dd, J=6.3, 11.7 Hz, 1H), 2.47 (s, 3H).

Toluene-4-sulfonic acid (2S)-6,7-dichloro-2,3-dihydro-benzo[1,4]dioxin-2-ylmethyl ester (8.0 g, 20.5 mmol) was combined with potassium phthalimide (6.1 g, 33 mmol) in DMF (75 mL) and heated to reflux for 1 h, cooled to room temperature and poured into vigorously stirring water (0.5 L) and then stirred 30 min. White solid was filtered and the solid was washed several times with water, 2% NaOH, and water again and then let air dry to yield (2S)-2-(6,7-dichloro-2,3-dihydro-benzo[1,4]dioxin-2-ylmethyl)-isoindole-1,3-dione (6.0 g, 80%) as a white powdery solid.

The white powdery solid was combined with hydrazine (1.06 g, 33 mmol) in EtOH (80 mL) and heated at reflux for 2 h, then cooled to room temperature. 1N HCl was added to adjust the reaction mixture's pH to pH 1.0 and the reaction mixture was then stirred for 15 min. White solid was filtered and washed with fresh EtOH (solid discarded) and the filtrate was evaporated in vacuo to a solid, which was partitioned between diethyl ether and dilute aqueous NaOH. The diethyl ether solution was dried (Na₂SO₄) and evaporated in vacuo to a yield a viscous oil of (2S)-2-aminomethyl-(6,7-dichloro-2,3-dihydro-benzo[1,4]dioxine).

¹H NMR (CDCl3): δ 6.98 (s, 1H), 6.96 (s, 1H), 4.25 (dd, J=2.0, 11.2 Hz, 1H), 4.15 (m, 1H), 4.0 (m, 1H), 2.97 (d, J=5.5 Hz, 2H)

A portion of the oil (3.8 g, 16 mmol) and sulfamide (3.1 g, 32.4 mmol) were refluxed in dioxane (100 mL) for 2 h and the crude product was purified by flash column chromatography (DCM:MeOH 20:1) to yield the title compound as a white solid, which was recrystallized from ethyl acetate/hexane to yield the title compound as a white crystalline solid.

MS [M−H]⁻ 311.0
mp 119-121° C.
[α]_D=−53.4° (c=1.17, M)
¹H NMR (DMSO-d6): δ 7.22 (s, 1H), 7.20 (s, 1H), 6.91 (bd s, 1H), 6.68 (bd s, 2H), 4.35 (m, 2H), 4.05 (dd, J=6.5, 11.5 Hz, 1H), 3.15 (m, 2H)
Elemental Analysis:
Elemental Analysis:

| Measured: | C, 34.52; H, 3.22; N, 8.95; Cl, 22.64; S, 10.24 |
| Calculated: | C, 34.64; H, 2.68; N, 8.87; Cl, 22.94; S, 10.35. |

Example 11

(2S)-(−)-N-(7-Amino-2,3-dihydro-benzo[1,4]dioxin-2-ylmethyl)-sulfamide (Compound #36)

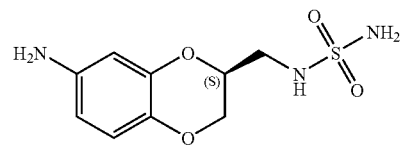

(2S)-(−)-N-(2,3-Dihydro-7-nitro-benzo[1,4]dioxin-2-ylmethyl)-sulfamide (1.2 g, 4.15 mmol), was prepared from 4-nitrocatechol according to the process outlined in Example 4. The (2S)-(−)-N-(2,3-Dihydro-7-nitro-benzo[1,4]dioxin-2-ylmethyl)-sulfamide, was then combined with 10% Pd/C in methanol (120 mL) and shaken under hydrogen atmosphere (39 psi) at room temperature for 3 h. The solids were filtered and washed with 10% M in DCM and the filtrate was evaporated in vacuo to yield crude product. The crude product was dissolved in 0.2 N HCl (25 mL), frozen and lyophilized to yield the title compound as a white flaky solid, as the corresponding hydrochloride salt.

MS (M+H)$^+$ 260

$^1$H NMR (DMSO d6): δ10.2 (bd s, 3H), 6.86 (m, 1H), 6.85 (s, 1H), 6.74 (dd, J=2.5, 8.4 Hz, 1H), 4.22 (m, 2H), 3.88 (dd, J=6.7, 11.4 Hz, 1H), 3.04 (m, 2H)

Example 12

(2S)-(−)-N-(7-Methyl-2,3-dihydro-benzo[1,4]dioxin-2-ylmethyl)-sulfamide (Compound #19)

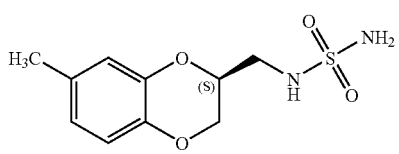

Title compound was prepared according to the procedure described in Example 4 above, starting with 4-methylcatechol, to yield a white solid, which was recrystallized from ethyl acetate/hexane to yield the title compound as a white solid.

MS [M−H]$^−$ 257

$^1$H NMR (CDCl3): δ 6.76 (m, 1H), 6.66 (m, 2H), 4.80 (m, 1H), 4.57 (bd s, 1H), 4.40 (m, 1H), 4.28 (m, 1H), 4.03 (dd, J=6.9, 11.4 Hz, 1H), 3.45 (m, 2H), 2.25 (s, 3H).

Elemental Analysis

| Calculated: | C, 46.50; H, 5.46; N, 10.85; S, 12.41 |
| Found: | C, 46.65; H, 5.60; N, 10.84; S, 12.61. |

Example 13

AKR/J Obese Mice In Vivo Assay

AKR/J mice are known in the art to be susceptible to diet-induced obesity. (Rossmeisl M, Rim J S, Koza R A, Kozak L P. Diabetes. 2003 August; 52(8):1958-66.)

Male AKR/J mice (~20 gram) at 4-5 weeks of age (Jackson Laboratories, Bar Harbor, Me.) were housed individually in a shoe-box cage at 21° C. with a 12-h light-dark cycle. The mice were fed with a high fat diet for 8 weeks to induce obesity. The composition of the diet by energy was 45% energy as fat, 20% as protein, and 35% as carbohydrate (Research Diets, D12451, New Brunswick, N.J.).

Obese mice with body weights between 35 and 46 grams were selected for the studies. Mice were randomized according to body weight into treatment groups at 13 weeks of age. The mice were orally gavaged once daily (0.2 ml at 1500-1700 hour) with vehicle control (0.5% methylcellulose, pH7.4) or vehicle containing Compound #8 (300 mg/kg). The body weights and food intake of the mice were monitored every few days. On day 11, the mice were anaesthetized with sodium pentobarbital (1 ml/kg, i.p, Sleepaway, Fort Dodge, Iowa). White adipose tissue (WAT) (retroperitoneal fat) and skeletal muscle (gastrocnemius and soleus muscle) were dissected and weighed.

Data shown below are expressed as mean and standard error calculated using 9-10 mice per treatment group. The 2 tailed Student's t-Tests were used for statistic analysis. All animal studies complied with the guideline of the Institutional Animal Care and Use Committee.

After 10-day treatment, Compound #8 treated mice showed greater weight loss compared to vehicle treated mice. The weight loss was accompanied with the loss of the white adipose tissue—there was a 26.6% reduction of retroperitoneal fat in Compound #8 treated mice relative to vehicle treated mice, with no significant changes in skeletal muscle mass. Thus the fat to lean mass ratio (white adipose tissue/skeletal muscle) decreased by 16.8% in Compound #8 treated mice compared to vehicle treated mice (vehicle: 8.9±0.4 vs Compound #8: 7.4±0.5, p<0.05). A reduction of food intake was also observed from day 4 to day 10 in Compound #8 treated mice relative to control animals. Compound #8 was also measured to delay gastric emptying at a statistically significant level (p<0.05).

A summary of the data for vehicle and Compound #8 treated mice measuring weight, food intake, fat and muscle mass as shown in Table 4, below.

TABLE 4

Obese Mice In Vivo Results

| | Weight Loss (g) | Food Intake (g) Day 4-10 | Retroperitoneal Fat Weight (g) | Skeletal Muscle Weight (g) |
|---|---|---|---|---|
| Vehicle | −0.7 ± 0.31 | 18.8 ± 0.67 | 0.64 ± 0.04 | 0.31 ± 0.01 |
| Compound #8 | −3.3 ± 0.34 p < 0.01 | 16.2 ± 0.68 p < 0.05 | 0.47 ± 0.04 p < 0.05 | 0.30 ± 0.01 |

Thus, the data show that Compound #8 was effective at promoting weight loss, wherein the loss was in fat rather than muscle mass and was further effective in decreasing food intake (i.e. suppressing appetite).

Example 14

Obesity In Vivo Assays

Compound #8 was suspended in 0.5% Methocel using a hand held homogenizer to reduce the particle size and a magnetic stir bar and stir plate to keep the particles homogeneously suspended throughout the dosing period. 0.5% Hydroxypropyl Methylcellulose (Methocel) used as vehicle/control.

Male AKR/J mice weighing between 35 to 46 grams were used for weight loss studies. AKR/J mice are susceptible to diet-induced obesity. Male AKR/J mice (average body weight of about 20 grams) at 4 to 5 weeks of age (obtained from Jackson Laboratories, Bar Harbor, Me.) were group housed, five per cage, in a shoebox cage at 21° C. with a 12 h light dark cycle. All of the mice were quarantined for a period of one week before transfer to the animal procedure room. The mice were fed a high fat diet for 8 weeks to induce obesity. The composition of the diet by energy was 45% energy as fat, 20% as protein, and 35% as carbohydrate (obtained from Research Diets, D12451, New Brunswick, N.J.). As a non-obese control, an additional group of mice that were age- and weight-matched was fed with a low fat diet (obtained from Research Diets, D12450B, New Brunswick, N.J.). Only mice that developed obesity, defined as a body weight between 35 and 46 grams, were selected for the weight loss studies. Animals were separated and single housed at least three days prior to the drug treatments to allow acclimation to the new surroundings.

The assay comprised two separate studies: In the first study, 10 mice were given vehicle control of 0.5% Methocel; 10 mice were treated with 300 mg/kg Compound #8 in vehicle; and 10 mice were dosed as positive control with 10 mg/kg sibutramine (a weight loss agent) in vehicle. In the second study, 48 mice were allocated into 4 treatment groups of 12 mice each. The four groups were then treated with 0.5% Methocel (vehicle), 10 mg/kg Compound #8, 30 mg/kg Compound #8, and 100 mg/kg Compound #8 in vehicle, respectively.

The mice were orally gavaged once daily (at 1500-1700 hour) with vehicle control (0.5% methocel, pH7.4) or vehicle containing Compound #8 for 10 days. The dosing volume was 5 mL/kg body weight (0.2 mL for 40 gram mice). Body weight and food intake of mice were monitored periodically throughout the studies. On Day 11, the mice were fasted for 4 hr during light cycle (food was removed 0600-1000 hour). A necropsy was done 18 hours after last dosing. The mice were anaesthetized with sodium pentobarbital (1 ml/kg, intraperitoneal [i.p.] injection, SleepAway, Fort Dodge, Iowa) and blood was drawn via cardiac puncture using an 1 mL syringe and collected into heparinized tubes. White adipose tissues (WAT) (retroperitoneal and inguinal fat pads), brown adipose tissue (BAT) and skeletal muscles (gastrocnemius and soleus muscle) and stomach contents were dissected and weighed. Plasma samples were obtained by centrifuging whole blood at 2000~3000 g for 10~20 minutes at 4° C. and stored at −20° C. for further measurement of insulin, HDL, LDL, and total cholesterol and triglyceride.

Blood glucose levels were measured with a glucometer (OneTouch UltraSmart, Lifescan, Milpitas, Calif.) after collecting two microliters of blood through tail puncture. Plasma insulin concentrations were measured by using rat/mouse insulin enzyme-linked immunosorbent assay (ELISA) kit (EZRMI-13K, LINCO Research, St. Charles, Mo.). Blood samples were diluted 1:4 in charcoal stripped mouse serum that was included in the ELISA kit. The rest of the procedure followed the manufacturers instruction. The total fluorescence was detected using an Orion 1 Microplate Luminometer (Berthold Detection Systems, Pforzheim, Germany). Plasma total cholesterol, high density lipoprotein (HDL), low density lipoprotein (LDL) and triglyceride concentrations were measured by using a Bayer ADVIA 1650 blood chemistry analyzer (Bayer HealthCare LLC, Diagnostic Division, Tarrytown, N.Y.). According to manufacturers protocol, cholesterol measurement was an enzymatic method utilizing cholesterol esterase and cholesterol oxidase conversion followed by a Trinder endpoint; Elimination/catalase method was used for HDL and LDL measurement; an enzymatic method with a Trinder endpoint was used for triglyceride measurement.

Data from the studies was analyzed using the standard two-tailed Student's t-test and are expressed in the tables below as means and standard errors. Fat/muscle ratios were calculated as: total weights of inguinal fat and retroperitoneal fat/muscle weight. Values listed in the tables represent the mean±SE (n=9~10).

The average body weight of AKR/J mice before the start of the high fat diet was 21.7±0.49 g. After eight weeks on the high fat diet, the average weight of the mice was 37.6±0.45 g. The mice with greatest weight gain were selected for dosing with Compound #8 or vehicle.

In the first study, and as shown in Table 5 below, mice treated with 300 mg/kg of Compound #8 showed significant weight loss, compared with vehicle treated mice after 10 days of dosing. The weight loss effects were observed 3 days after treatment and lasted until the end of the study. Significant suppression of food intake was also found three days after treatment with Compound #8 compared to vehicle. In contrast, mice treated with the anti-obesity agent sibutramine lost weight after 3 days treatment, but showed no difference in weight at the end of the study compared to control mice. A reduction of food intake in sibutramine treated mice was also seen from day 0 to Day 3 but not from Day 4 through Day 9. Total stomach content, measured at the end of the study, was significantly greater (0.27±0.05 g, $p<0.05$) with Compound #8 treatment compared to vehicle treatment (0.16±0.02 g).

TABLE 5

| Treatment | Weight loss (g) | | | Intake of high fat diet (g) | |
| --- | --- | --- | --- | --- | --- |
| | Day 4 | Day 8 | Day 10 | Day 0-3 | Day 4-7 |
| Vehicle | −0.2 ± 0.1 | −0.3 ± 0.3 | −0.7 ± 0.3 | 9.3 ± 0.2 | 12.9 ± 0.5 |
| Sibutramine | −2.0 ± 0.2*** | −1.2 ± 0.4 | −1.2 ± 0.5 | 6.5 ± 0.3** | 14.4 ± 0.7 |
| Compound #8 @ 300 mg/kg | −0.3 ± 0.3 | −2.5 ± 0.3*** | −3.3 ± 0.3*** | 10.0 ± 0.4 | 10.6 ± 0.4* |

*$p < 0.05$,
**$p < 0.01$,
***$p < 0.001$ versus vehicle control, respectively.

Mice treated with Compound #8 also showed reduced white adipose tissue weight compared with vehicle treatment after 10 days of dosing. This resulted in a lower ratio of fat to muscle weight in the Compound #8 treated group of mice, as shown in Table 6, below. In Table 6 below, the ratio of fat to muscle was calculated as: total weights of inguinal fat and retroperitoneal fat/muscle weight.

TABLE 6

| Treatment | Epididymal fat (g) | Retroperitoneal fat (g) | Muscle (g) | Brown Adipose Tissue (g) | Ratio (fat/muscle) |
| --- | --- | --- | --- | --- | --- |
| Vehicle | 2.08 ± 0.11 | 0.64 ± 0.04 | 0.31 ± 0.01 | 0.13 ± 0.01 | 8.90 ± 0.42 |
| Sibutramine | 1.76 ± 0.11* | 0.61 ± 0.07 | 0.31 ± 0.01 | 0.14 ± 0.01 | 7.67 ± 0.59 |
| Compound #8 @ 300 mg/kg | 1.73 ± 0.10* | 0.47 ± 0.04* | 0.30 ± 0.01 | 0.22 ± 0.09 | 7.42 ± 0.54* |

*$p < 0.05$ versus vehicle control, respectively.

In the second dose response study, as shown in Table 7 below, there was no significant (P>0.05) weight loss or food intake suppression in the mice treated with 10, 30, and 100 mg/kg of Compound #8. In this study, tissue was not collected and as such values from fat and muscle were not determined.

TABLE 7

| Treatment | Weight loss (g) | | | Total intake of high fat diet (g) |
| --- | --- | --- | --- | --- |
| | Day 4 | Day 7 | Day 10 | Day 1-10 |
| Vehicle | −0.3 ± 0.1 | −0.3 ± 0.2 | −0.4 ± 0.2 | 27 ± 0.5 |
| Compound #8 @ 10 mg/kg | 0.1 ± 0.1 | 0.2 ± 0.2 | 0.3 ± 0.3 | 28 ± 0.5 |
| Compound #8 @ 30 mg/kg | 0.1 ± 0.1 | 0.0 ± 0.2 | −0.4 ±0.2 | 28 ± 0.5 |
| Compound #8 @ 100 mg/kg | 0.2 ± 0.1 | 0.2 ± 0.3 | 0.1 ± 0.2 | 28 ± 0.6 |

Example 15

As a specific embodiment of an oral composition, 100 mg of the Compound #8 prepared as in Example 7 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method for treating obesity, promoting weight loss or suppressing appetite comprising administering to a subject in need thereof, a therapeutically effective amount of a compound of formula (I)

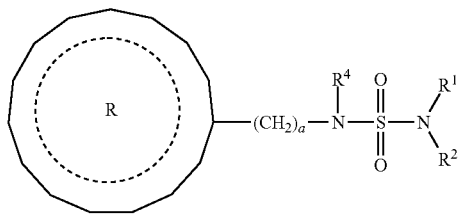

(I)

wherein $R^1$ and $R^2$ are each independently selected from the group consisting of hydrogen and lower alkyl;

$R^4$ is selected from the group consisting of hydrogen and lower alkyl;

a is an integer from 1 to 2;

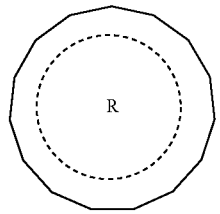

is

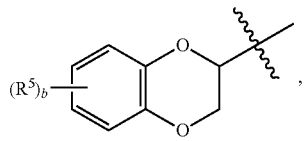

wherein b is an integer from 0 to 4; and wherein
each $R^5$ is independently selected from the group consisting of chloro, fluoro, bromo and methyl;
or a pharmaceutically acceptable salt thereof.

2. The method as in claim 1, wherein
$R^1$ and $R^2$ are each independently selected from the group consisting of hydrogen and lower alkyl;
$R^4$ is selected from the group consisting of hydrogen and lower alkyl;
a is an integer from 1 to 2;

is

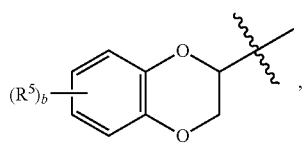

wherein b is an integer from 0 to 2; and wherein;
each $R^5$ is independently selected from the group consisting of chloro, fluoro, bromo and methyl;
or a pharmaceutically acceptable salt thereof.

3. The method as in claim 2, wherein
$R^1$ and $R^2$ are each independently selected from the group consisting of hydrogen and lower alkyl;
$R^4$ is selected from the group consisting of hydrogen and lower alkyl;
a is an integer from 1 to 2;

is

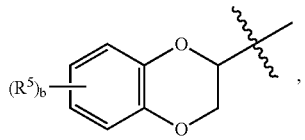

wherein b is an integer from 0 to 2; and wherein;

each $R^5$ is independently selected from the group consisting of chloro, fluoro, bromo and methyl;

or a pharmaceutically acceptable salt thereof.

4. The method as in claim 3, wherein $R^1$ and $R^2$ are each independently selected from the group consisting of hydrogen and lower alkyl;

$R^4$ is selected from the group consisting of hydrogen and methyl;

a is an integer from 1 to 2;

is selected from the group consisting of 2-(2,3-dihydro-benzo[1,4]dioxinyl), 2-(6 chloro-2,3-dihydro-benzo[1,4]dioxinyl), 2-(6-fluoro-2,3-dihydro-benzo[1,4]dioxinyl), 2-(5 fluoro-2,3-dihydro-benzo[1,4]dioxinyl), 2-(7-chloro-2,3-dihydro-benzo[1,4]dioxinyl), 2 (7 nitro-2,3-dihydro-benzo[1,4]dioxinyl), 2-(7-methyl-2,3-dihydro-benzo[1,4]dioxinyl), 2-(5-chloro-2,3-dihydro-benzo[1,4]dioxinyl), 2-(6-bromo-2,3-dihydro-benzo[1,4]dioxinyl), 2-(6,7-dichloro-2,3-dihydro-benzo[1,4]dioxinyl), and 2-(8-chloro-2,3-dihydro-benzo[1,4]dioxinyl);

or a pharmaceutically acceptable salt thereof.

5. The method as in claim 4, wherein $R^1$ and $R^2$ are each independently selected from the group consisting of hydrogen and methyl;

$R^4$ is selected from the group consisting of hydrogen and methyl;

a is an integer from 1 to 2;

is selected from the group consisting of 2 (2,3-dihydro-benzo[1,4]dioxinyl), 2 (6 chloro-2,3-dihydro-benzo[1,4]dioxinyl), 2-(7-chloro-2,3-dihydro-benzo[1,4]dioxinyl), 2-(7-methyl-2,3-dihydro-benzo[1,4]dioxinyl), 2-(6-bromo-2,3-dihydro-benzo[1,4]dioxinyl) and 2-(6,7-dichloro-2,3-dihydro-benzo[1,4]dioxinyl);

or a pharmaceutically acceptable salt thereof.

6. The method of claim 1, wherein the compound of formula (I) is selected from the group consisting of (2S)-(−)-N-(6-chloro-2,3-dihydro-benzo[1,4]dioxin-2-ylmethyl)-sulfamide; and pharmaceutically acceptable salts thereof.

7. A method of treating obesity comprising administering to a subject in need thereof a therapeutically effective amount of a compound selected from the group consisting (2S)-(−)-N-(6-chloro-2,3-dihydro-benzo[1,4]dioxin-2-ylmethyl)-sulfamide; and pharmaceutically acceptable salts thereof.

8. A method of promoting weight loss comprising administering to a subject in need thereof a therapeutically effective amount of a compound selected from the group consisting (2S)-(−)-N-(6-chloro-2,3-dihydro-benzo[1,4]dioxin-2-ylmethyl)-sulfamide; and pharmaceutically acceptable salts thereof.

9. A method of suppressing appetite comprising administering to a subject in need thereof a therapeutically effective amount of a compound selected from the group consisting (2S)-(−)-N-(6-chloro-2,3-dihydro-benzo[1,4]dioxin-2-ylmethyl)-sulfamide; and pharmaceutically acceptable salts thereof.

10. A method for treating obesity, promoting weight loss or suppressing appetite comprising administering to a subject in need thereof a therapeutically effective amount of a compound of formula

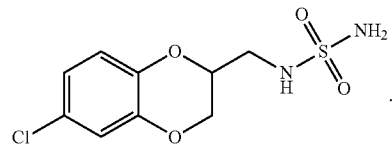 [SMILES: NS(=O)(=O)NCC1COc2cc(Cl)ccc2O1]

* * * * *

UNITED STATES PATENT AND TRADEMARK OFFICE
CERTIFICATE OF CORRECTION

| | | |
|---|---|---|
| PATENT NO. | : 8,492,431 B2 | Page 1 of 1 |
| APPLICATION NO. | : 11/611938 | |
| DATED | : July 23, 2013 | |
| INVENTOR(S) | : Smith-Swintosky et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 839 days.

Signed and Sealed this
Tenth Day of February, 2015

Michelle K. Lee
*Deputy Director of the United States Patent and Trademark Office*